(12) United States Patent
Soosalu et al.

(10) Patent No.: US 10,667,766 B2
(45) Date of Patent: Jun. 2, 2020

(54) METHOD AND SYSTEM FOR MONITORING MULTIPLE PATIENT PARAMETERS ON A TOUCHSCREEN

(71) Applicant: General Electric Company, Schenectady, NY (US)

(72) Inventors: Milvi Kristiina Soosalu, Espoo (FI); Virpi Kristiina Lahdenmaki, Helsinki (FI)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/797,905

(22) Filed: Oct. 30, 2017

(65) Prior Publication Data

US 2019/0125278 A1    May 2, 2019

(51) Int. Cl.
| | |
|---|---|
| *G06F 3/048* | (2013.01) |
| *A61B 5/00* | (2006.01) |
| *G06F 3/0488* | (2013.01) |
| *G06T 11/20* | (2006.01) |
| *A61B 5/0205* | (2006.01) |
| *G06F 3/0484* | (2013.01) |

(52) U.S. Cl.
CPC .......... *A61B 5/7475* (2013.01); *A61B 5/0022* (2013.01); *A61B 5/0205* (2013.01); *A61B 5/746* (2013.01); *G06F 3/04883* (2013.01); *G06T 11/206* (2013.01); *G06F 3/04842* (2013.01); *G06F 2203/04808* (2013.01)

(58) Field of Classification Search
None
See application file for complete search history.

(56) References Cited

U.S. PATENT DOCUMENTS

| | | | |
|---|---|---|---|
| 5,942,986 A | * | 8/1999 | Shabot ................ G06F 19/3418 340/7.29 |
| 8,698,741 B1 | | 4/2014 | Wang et al. |
| 9,141,270 B1 | | 9/2015 | Stuart et al. |
| 9,507,486 B1 | | 11/2016 | Reed et al. |
| 9,665,264 B1 | | 5/2017 | Janiak |

(Continued)

OTHER PUBLICATIONS

Bragdon et al. "Experimental Analysis of Touch-Screen Gesture Designs in Mobile Environments" CHI (2011) 10 pages.

(Continued)

*Primary Examiner* — Sanchita Roy
(74) *Attorney, Agent, or Firm* — The Small Patent Law Group LLC; Dean D. Small

(57) ABSTRACT

Handheld patient-monitoring device is provided that includes a touchscreen having a display area. The touchscreen is configured to present a first chart section in the display area of the touchscreen. The device is also configured to detect an input gesture on the touchscreen that is indicative of a swipe along the touchscreen. The device is also configured to replace, in response to detecting the input gesture, the first chart section with a second chart section such that the second chart section is presented in the display area and the first chart section is not presented in the display area. The second chart section has at least one parameter region that displays information relating to a respective patient parameter. Replacement of the first chart section with the second chart section is visually indicated to the user.

17 Claims, 15 Drawing Sheets

(56) References Cited

U.S. PATENT DOCUMENTS

| | | | | |
|---|---|---|---|---|
| 2006/0085227 A1* | 4/2006 | Rosenfeld | ............ | G16H 50/20 |
| | | | | 705/2 |
| 2009/0054743 A1* | 2/2009 | Stewart | ............ | G16H 15/00 |
| | | | | 600/301 |
| 2010/0050085 A1* | 2/2010 | Blike | ............ | A61B 5/083 |
| | | | | 715/738 |
| 2010/0064374 A1* | 3/2010 | Martin | ............ | G16H 40/63 |
| | | | | 726/27 |
| 2010/0083164 A1* | 4/2010 | Martin | ............ | G16H 40/63 |
| | | | | 715/781 |
| 2010/0235782 A1* | 9/2010 | Powell | ............ | G06F 19/3418 |
| | | | | 715/809 |
| 2012/0075103 A1* | 3/2012 | Powell | ............ | G06F 19/3418 |
| | | | | 340/573.1 |
| 2013/0162433 A1* | 6/2013 | Muhsin | ............ | G08B 25/008 |
| | | | | 340/573.1 |
| 2014/0033103 A1* | 1/2014 | Boyer | ............ | G06F 3/0488 |
| | | | | 715/771 |
| 2014/0132413 A1* | 5/2014 | Fox | ............ | A61B 5/0022 |
| | | | | 340/573.1 |
| 2014/0351738 A1 | 11/2014 | Kokovidis et al. | | |
| 2015/0100892 A1* | 4/2015 | Cronin | ............ | G06Q 10/06 |
| | | | | 715/747 |
| 2015/0301717 A1* | 10/2015 | Wekell | ............ | G16H 15/00 |
| | | | | 715/835 |
| 2016/0345874 A1* | 12/2016 | Raisoni | ............ | A61B 5/002 |
| 2018/0232494 A1* | 8/2018 | Leppala | ............ | G06F 3/04845 |

OTHER PUBLICATIONS

International Search Report and Written Opinion for corresponding PCT Application No. PCT/US2018/057227 dated Feb. 9, 2019 (11 pages).

* cited by examiner

METHOD AND SYSTEM FOR MONITORING MULTIPLE PATIENT PARAMETERS ON A TOUCHSCREEN

BACKGROUND

The subject matter herein relates generally to patient monitoring systems and methods, and more particularly, to patient monitoring systems and methods that monitor multiple parameters on a touchscreen.

Patient-monitoring systems are configured to receive physiological data from a patient, analyze the physiological data, and communicate information to a healthcare provider so that the healthcare provider may assess a condition of the patient. Conventional monitoring systems include one or more detection devices that detect the physiological data and a user display that presents the information to the healthcare provider. The information includes recognizable physiological parameters relating to the patient (referred to herein as "patient parameters") that the healthcare provider may use to assess a health status or condition of the patient. Non-limiting examples of these patient parameters include heart rate, blood pressure, respiration rate, an estimate of the amount of oxygen in the blood ($SpO_2$), an estimate of the amount of carbon dioxide in the blood ($CO_2$%), electrocardiographic (ECG) data, auditory evoked potentials, and electroencephalogram (EEG) data. Assessing a health status or condition of the patient often includes simultaneously analyzing multiple patient parameters. The number and selection of patient parameters can sometimes be specific to the patient.

Conventional patient-monitoring systems today include user displays that present a health-monitoring chart to a user of the system. Health-monitoring charts are configured to appear similar to the strip charts created by the traditional systems and may comprise waveform displays and/or a set of parameter values having a predetermined appearance (e.g., arrangement and coloring). As one example, the waveforms may be shown with aspect ratios that match the aspect ratios of established standards. More recently, however, health-monitoring charts are being displayed on smaller and more portable devices (e.g., portable computers, tablets, smartphones), which can create challenges for displaying the health-monitoring chart.

BRIEF DESCRIPTION

In an embodiment, a handheld patient-monitoring device is provided that includes a touchscreen having a display area. The touchscreen is configured to present a health-monitoring chart to a user. The health-monitoring chart is based on physiological data detected from a patient. The patient-monitoring device also includes one or more processors configured to execute programmed instructions stored in memory. The one or more processors, when executing the programmed instructions, is configured to present a first chart section in the display area of the touchscreen. The first chart section has parameter regions that include information relating to respective patient parameters. The one or more processors is also configured to detect an input gesture on the touchscreen that is indicative of a swipe along the touchscreen. The input gesture extends generally in a swipe direction for at least a predetermined distance along the touchscreen. The one or more processors is also configured to replace, in response to detecting the input gesture, the first chart section with the second chart section such that the second chart section is presented in the display area and the first chart section is not presented in the display area. The second chart section has at least one parameter region that displays information relating to a respective patient parameter. Replacement of the first chart section with the second chart section is visually indicated to the user.

In some aspects, the one or more processors is also configured to determine that one of the patient parameters has become significant, wherein presenting the first chart section in the display area includes displaying a parameter alert on the touchscreen. The parameter alert identifies the patient parameter that has become significant.

Optionally, the second chart section may be a condition-specific chart section. In response to determining that one of the patient parameters has become significant, the one or more processors may be configured to generate the condition-specific chart section. The condition-specific chart section is based on the patient parameter that has become significant. The condition-specific chart section includes additional information that is not presented in the first chart section. Optionally, the condition-specific chart section includes a parameter signal line plotted with respect to horizontal and vertical axes. The horizontal axis represents time and the vertical axis represents values of a patient parameter.

In some aspects, the patient parameter that has become significant is highlighted to the user in the second chart section.

In some aspects the one or more processors are also configured to, in response to displaying the parameter alert on the touchscreen, automatically replace the first chart section with the second chart section.

In some aspects, replacing, in response to detecting the input gesture, the first chart section with the second chart section includes indicating that the first chart section is shifting in the swipe direction.

In some aspects, the first chart section and the second chart section appear as separate and discrete sections.

In an embodiment, a method for monitoring a condition of a patient is provided. The method includes providing a health-monitoring chart to a patient-monitoring device for presenting in a display area of a touchscreen of the patient-monitoring device. The health-monitoring chart includes a first chart section and a second chart section. The method also includes presenting the first chart section in the display area of the touchscreen. The first chart section has parameter regions that include information relating to respective patient parameters. The method also includes detecting an input gesture on the touchscreen that is indicative of a swipe along the touchscreen. The input gesture extends generally in a swipe direction for at least a predetermined distance along the touchscreen. The method may also include replacing, in response to detecting the input gesture, the first chart section with the second chart section such that the second chart section is presented in the display area and the first chart section is not presented in the display area. The second chart section has at least one parameter region that displays information relating to a respective patient parameter, wherein replacement of the first chart section with the second chart section is visually indicated to the user.

In some aspects, the method also includes determining that one of the patient parameters has become significant, wherein presenting the first chart section in the display area includes displaying a parameter alert on the touchscreen. The parameter alert identifies the patient parameter that has become significant.

In some aspects, the second chart section is a condition-specific chart section. The method also includes generating the condition-specific chart section in response to determining that one of the patient parameters has become significant. The condition-specific chart section is based on the patient parameter that has become significant. The condition-specific chart section includes additional information that is not presented in the first chart section.

Optionally, the condition-specific chart section includes a parameter signal line plotted with respect to horizontal and vertical axes. The horizontal axis represents time and the vertical axis representing values of a patient parameter.

In some aspects, the patient parameter that has become significant is highlighted to the user in the second chart section.

In some aspects, the one or more processors are also configured to, in response to displaying the parameter alert on the touchscreen, automatically replace the first chart section with the second chart section.

In some aspects, the first chart section and the second chart section appear as separate and discrete sections.

In an embodiment, a non-transitory computer-readable storage medium is provided that has computer executable code to present a first chart section in a display area of a touchscreen. The first chart section has parameter regions that include information relating to respective patient parameters. The computer executable code is also configured to receive an input gesture from a gesture recognizer that is indicative of a swipe along the touchscreen and replace, in response to receiving the input gesture, the first chart section with the second chart section such that the second chart section is presented in the display area and the first chart section is not presented in the display area. The second chart section has at least one parameter region that displays information relating to a respective patient parameter. The computer executable code is also configured to indicate, in the display area, that the second chart section has replaced or is replacing the first chart section.

In some aspects, the computer executable code is also configured to determine that one of the patient parameters has become significant, wherein presenting the first chart section in the display area includes displaying a parameter alert on the touchscreen. The parameter alert identifies the patient parameter that has become significant.

In some aspects, the second chart section is a condition-specific chart section. The computer executable code may be configured to generate the condition-specific chart section in response to determining that one of the patient parameters has become significant. The condition-specific chart section may be based on the patient parameter that has become significant. The condition-specific chart section includes additional information that is not presented in the first chart section.

In some aspects, the condition-specific chart section includes a parameter signal line plotted with respect to horizontal and vertical axes. The horizontal axis representing time and the vertical axis representing values of a patient parameter.

In some aspects, the first chart section and the second chart section appear as separate and discrete sections.

In an embodiment, a patient-monitoring device is provided that includes a touchscreen having a display area. The touchscreen is configured to present a health-monitoring chart to a user. The health-monitoring chart is based on physiological data detected from a patient. The patient-monitoring device also includes one or more processors configured to execute programmed instructions stored in memory. The one or more processors, when executing the programmed instructions, is configured to present a chart section in the display area of the touchscreen. The chart section has parameter regions that include information relating to respective patient parameters. The one or more processors is also configured to detect an input gesture on the touchscreen. The input gesture may be indicative of, for example, a swipe or one or more taps. The one or more processors is also configured to replace, in response to detecting the input gesture, the chart section with another chart section such that the other chart section is presented in the display area. The other chart section has at least one parameter region that displays information relating to a respective patient parameter. Replacement of the chart section with the other chart section is visually indicated to the user.

Optionally, the other chart section may be a condition-specific chart section. The condition-specific chart section may be based on a patient parameter that has become significant. Optionally, the input gesture may indicate that the user has touched a parameter alert displayed in the chart section. The one or more processors may be configured to replace the chart section with the condition-specific chart section in response to detecting the input gesture.

In some aspects, the health-monitoring chart includes multiple predetermined chart sections. The one or more processors may detect input gestures to transition to the other chart sections. Optionally, the one or more processors may automatically replace one chart section with another chart section.

In an embodiment, a method for monitoring a condition of a patient is provided. The method includes providing a health-monitoring chart to a patient-monitoring device for presenting in a display area of a touchscreen of the patient-monitoring device. The health-monitoring chart includes a chart section. The method also includes presenting the chart section in the display area of the touchscreen. The chart section has parameter regions that include information relating to respective patient parameters. The method also includes detecting an input gesture on the touchscreen. The input gesture may be indicative of, for example, a swipe or one or more taps. The method may also include replacing, in response to detecting the input gesture, the chart section with another chart section such that the other chart section is presented in the display area and the chart section (originally-presented chart section) is not presented in the display area. The other chart section has at least one parameter region that displays information relating to a respective patient parameter, wherein replacement of the chart section with the other chart section is visually indicated to the user.

DETAILED DESCRIPTION

Figure 1:
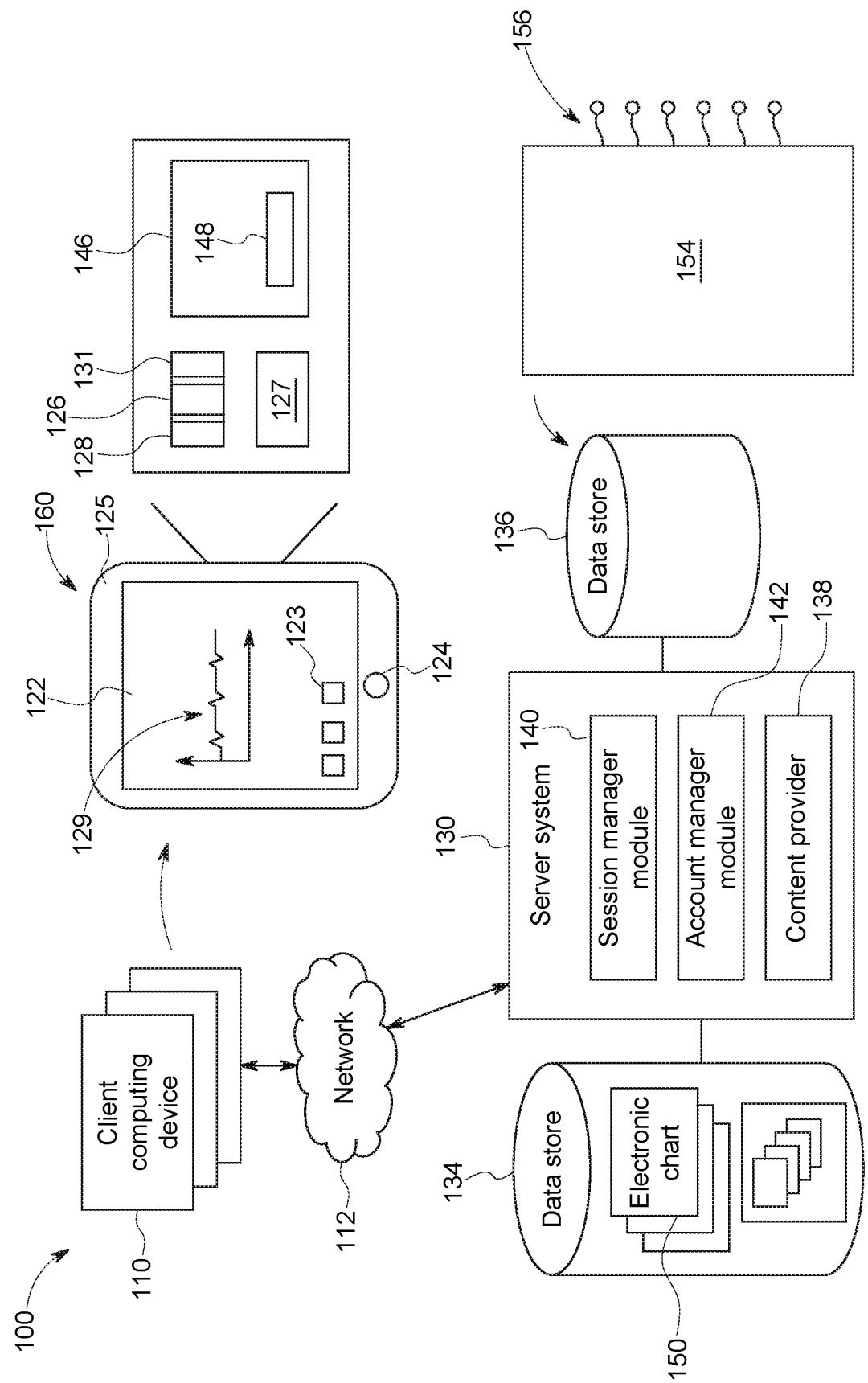
FIG. 1 is a block diagram of an exemplary system in accordance with an embodiment.

Embodiments described herein include systems and methods that display health-monitoring charts having multiple patient parameters on a display area of a touch-sensitive screen (hereinafter referred to as a "touchscreen"). The health-monitoring charts include parameter regions. Parameter regions are portions of the health-monitoring chart that are displayed to the user. The parameter regions communicate information to the user regarding respective patient parameters. Non-limiting examples of patient parameters include heart rate, blood pressure, respiration rate or other ventilation parameters, an estimate of the amount of oxygen in the blood ($SpO_2$), an estimate of the amount of carbon dioxide in the blood ($CO_2\%$), electrocardiographic (ECG) data, auditory evoked potentials, and electroencephalogram (EEG) data. The health-monitoring chart is designed to show multiple patient parameters for at least some of the time.

One or more embodiments may display real-time information for at least one of the parameters shown in the display area. As used herein, the terms "real-time information," "real-time data," and the like, mean that the information or data are updated at a sufficient frequency so that a healthcare provider may assess a current health status of the patient. Some patient parameters may be updated continuously or near continuously, while other parameters are updated less frequently (e.g., every 10 seconds or 30 seconds). The term includes delays that are inherent with automated processing.

The parameter regions include value areas that display a current or present value of the corresponding patient parameter. The value may be represented by alphanumeric text, which may include letters, numbers, or other text-like symbols (e.g., Greek or Roman letters). The value areas may have predetermined display characteristics. For example, the text may have a predetermined size (e.g., height, width, or both), aspect ratio, font, and/or position within the value area or relative to other values.

Optionally, the health-monitoring charts may also include signal lines representing certain patient parameters over time. As used herein, a "signal line" includes a line plotted along a two-dimensional graph that represents a dynamic patient parameter as time progresses. The signal line may be referred to as a waveform, tracing or trace, or trend line. The signal line is not required to be a solid, continuous line throughout. For example, a single graph region may include multiple, overlapping signal lines. One or more of the signal lines may be a solid line and one or more of the other signal lines may be a dashed line. Different dashed lines may have different dashing patterns.

In some embodiments, the signal line is a compressed waveform that illustrates a trend of the patient parameter. Using ST-segment monitoring as an example, the signal line may be a compressed form of a continuous waveform that represents numerous heart beats over an extended period of time (e.g., several minutes, multiple hours, or one or more days). In such instances, discrete electrical stages or events of each heart beat (e.g., peaks and valleys of a wave) may not be identifiable due to the compression of the waveform. In other embodiments, however, the signal line may be a continuous waveform for a shorter period of time (e.g., 1-10 seconds) such that discrete electrical events of an individual heart beat can be identified.

Signal lines may appear as waveforms that form a characteristic patterns of the patient parameter. For example, electrocardiography (ECG) waveforms may include PQRST wave patterns that provide useful information to a user for identifying a health status of an individual. The waveforms may be configured to have aspect ratios (or other waveform characteristics) that are effectively equal to standard aspect ratios (or other waveform characteristics) for a physiological parameter-of-interest.

Physiological information displayed by embodiments described herein may relate to, for example, a heart rate, body temperature, blood pressure, respiratory rate, electrical activity, intrauterine pressure, or other parameter that may be analyzed to provide meaningful information regarding a human or animal condition. Waveforms are typically plotted as a function of time, but it is contemplated that other waveforms may be plotted as a function of a non-temporal parameter. Although one or more parameters may be represented by waveforms, it should be understood that one or more other parameters are not represented by waveforms. In some embodiments, the health-monitoring chart does not display any waveforms.

Embodiments are also configured to detect input gestures on the touchscreen. The input gestures may be provided by a digit (e.g., finger) or a tool (e.g., stylus or designated glove). Non-limiting examples of input gestures that may be detected by one or more embodiments includes (1) a single tap in which the display area is touched by a single digit or tool; (2) a multi-tap in which two or more touches are detected in quick succession at essentially the same area (e.g., by the same finger or same tool); (3) a long press in which the display area is touched for a predetermined period of time; (4) press-and-tap in which one long press is detected, followed by a different touch (e.g., by another finger); (4) two-finger tap; (5) a swipe in which the display area is continuously touched along a predetermined distance of the screen and then released; (6) a pinch in which two touches are detected followed by at least one swipe; (7) a rotating two-finger tap; (8) and a two-finger pan.

Input gestures cause data to be communicated to an appropriate destination (e.g., controller or application program). Input gestures may be composite gestures in which multiple notifications or communications are sent to the application as the display area is touched. Composite gestures may include a swipe, a pinch, a rotate, or a two-finger tap. Input gestures may also be discrete gestures that send only a single notification to the application. Discrete gestures may include a tap, a multi-tap, a long press, a press-and-tap, or a two-finger tap.

The input gestures may be detected by a touch controller of the touchscreen (or the communication device) and communicated to a gesture recognizer. A touch event is an event generated by the touch controller in response to detecting a touch along the display area. Each touch event may be communicated with various types of information about the touch event, such as the type of touch event (touch, move, or release), the timestamp of the event, the coordinates of the touch, and an orientation of the device. The orientation of the device may be determined by an accelerometer of the device.

In particular embodiments, the gesture recognizer is a self-contained state machine of the device that progresses through various states in reaction to the input gestures that are detected. Depending on the input gesture, a gesture recognizer may interpret multiple touch events in order to detect a single input gesture. For example, a gesture recognizer may transition through multiple states before prior to determining the particular input gesture. In some embodiments, the gesture recognizer issues a gesture callback to the application in use. Applications may be programmed to receive and respond to predetermined input gestures.

Embodiments are configured to detect predetermined input gestures. For example, an input gesture that is indicative of a swipe by the user along the touchscreen may be detected and communicated to the application. In response to detecting the input gesture, embodiments may change the health-monitoring chart by transitioning a first chart section from the touchscreen and a second chart section into the touchscreen such that the second chart section is presented on the touchscreen and the first chart section is not presented on the touchscreen.

Embodiments may alert the user (e.g., healthcare provider) that a patient parameter has become significant. A patient parameter may be determined to be "significant" based upon a predetermined standard. As used herein, the term "significant" does not require clinical significance. Instead, the term means that the value is noteworthy or worthy of the attention of a user of the system. The predetermined standard may be an algorithm and/or one or more predetermined conditions. In some cases, the predetermined standard is an established standard within a medical field. In other cases, the predetermined standard may be proprietary. In some cases, the predetermined standard may be patient-specific such that the algorithm and/or conditions are particularly tailored for a patient. Optionally, the predetermined standard may be modified by the user of the system or entirely provided by a user of the system. For example, the user may change an upper limit to which the patient parameter will be compared, change a lower limit to which the patient parameter will be compared, and/or change an operating range to which the patient parameter will be compared. Optionally, the upper limit, the lower limit, and/or the operating range may have default values when the system is initially executed. In other embodiments, the predetermined standards may be entirely provided by the user. For example, the user may select a formula or enter a formula into the system. The formula may use the patient parameter, among other parameters or factors, as an input to determine whether the patient parameter is significant.

To illustrate some examples, a patient parameter may be significant if at least one of the following occurs: (a) the patient parameter has exceeded a designated value (e.g., exceeded an upper limit); (b) a patient parameter is below a designated value (e.g., below a lower limit); or (c) a patient parameter is not within a designated operating range, which may also be referred to as out-of-range. In some embodiments, a value is significant only if multiple conditions are satisfied. For example, a patient parameter may be determined to be significant if (a), (b), or (c) are satisfied and if other conditions are satisfied. A value may be significant only if one or more conditions are satisfied and a signal quality of the patient parameter is sufficient and/or other patient parameters have exceeded a designated value, fallen below a designated value, or are within a designated operating range. In some embodiments, a value is significant only if the patient parameter has satisfied (a), (b), or (c) for at least a minimum amount of time. For example, a value of a patient parameter may not be determined to be significant until the value has been above the upper limit for at least five seconds. Similarly, a value of a patient parameter may not be determined to be significant until the value has been below the lower limit for at least five seconds.

Alternatively or in addition to one or more of the above, a value may be significant only if the patient parameter has satisfied (a), (b), or (c) for at least a minimum number of events. For example, a value of a patient parameter may not be determined to be significant until the value has been above the upper limit for at least three heart beats. Similarly, a value of a patient parameter may not be determined to be significant until the value has been below the lower limit for at least three heart beats.

In some embodiments, a value may be significant if one or more of the following occurs: (a) the patient parameter has not exceeded a designated value (e.g., has not exceeded an upper limit); (b) a patient parameter is above a minimum value (e.g., above a lower limit); or (c) a patient parameter is within a designated operating range.

It should be understood that the above predetermined standards are examples of specific embodiments and other predetermined standards may be used for other embodiments. Other predetermined standards may include more complex algorithms that are based upon a number of patient parameters. The predetermined standards may also be based on other variables, including information that is not a parameter monitored by the system. For example, the predetermined standards may be a function of patient information (e.g., height, weight, medical history).

Accordingly, the predetermined standard for determining whether a patient parameter is significant may be a simple condition (e.g., a comparison to a limit) or may be a more complex calculation (e.g., an algorithm having multiple variables). The predetermined standard may be set by the system (e.g., stored within software), modified by the user, or entirely provided by the user. For embodiments that display multiple patient parameters, each of the patient parameters may have a respective predetermined standard that may or may not be different from the predetermined standards of other patient parameters.

In particular embodiments, multiple patient parameters are represented in the health-monitoring chart to form a multi-parameter record over an extended period of time (or time frame). By way of example, the time frame may be at least one minute, at least ten minutes, at least twenty minutes, at least one hour, at least three hours, or more. A healthcare provider may be able to simultaneously view and consider the significant moments of the multiple patient parameters over the time frame in order to assess a health status of the patient. Optionally, the user may view a history of one or more patient parameters for an extended period of time (e.g., several minutes to hours).

The systems and methods set forth herein may present (e.g., show or display) a historical record of the patient. The historical record may indicate moments within an extended period of time in which the patient had a healthy status and, if applicable, may show moments in which a patient parameter is significant (e.g., concerning or worthy of a healthcare provider's consideration). The significant moments may be identified using predetermined standards. In some embodiments, the system and methods are directed to assessing a cardiac condition of a patient. The physiological data received by the system is ECG data. Embodiments may simultaneously show the histories of multiple ECG leads to assess the cardiac condition of the patient. More specifically, embodiments may enable the healthcare provider to quickly identify when and which ECG leads have significant values and for how long the ECG leads had significant values. By way of example, embodiments may facilitate identifying the onset of an anterior ST segment elevation myocardial infarction (or anterior STEMI).

As used herein, the phrase "a plurality of parameter regions [having a recited feature]" or "multiple parameter regions [having a recited feature]" (and similar phrases) does not necessarily mean each and every parameter region that the health-monitoring chart may have or that a display area may display. For example, a health-monitoring chart may include other parameter regions that do not have the recited feature.

At least one technical effect of various embodiments includes providing a health-monitoring chart that enables the user to view multiple parameters on a touchscreen to assess a health-status of the patient. In some implementations, it may be undesirable to display each and every patient parameter that is being monitored in the display area. A technical effect for at least some embodiments may include presenting one or more parameter regions on one chart section and presenting one or more other parameter regions on a different chart section (or chart sections). Embodiments may enable a healthcare provider to quickly transition from one chart section to another. Embodiments may also enable the healthcare provider to identify the patient parameter that has become significant more quickly. Another technical effect may include notifying a user that a patient parameter is significant.

In particular embodiments, at least one other technical effect includes assembling a condition-specific chart section, in response to determining that a patient parameter is significant, in which the condition-specific chart section includes the significant patient parameter and other relevant patient parameters. The significant patient parameter and other relevant patient parameters may be those patient parameters that are typically reviewed to assess a predetermined condition. For example, if an ECG parameter is determined to be significant, a condition-specific chart section may include the ECG parameter, other ECG parameters, ST values, and historical trends. The condition-specific chart section may be referred to as a "condition-specific chart section." The condition-specific chart section is based on the patient parameter that has become significant.

As used herein, an element or step recited in the singular and proceeded with the word "a" or "an" should be understood as not excluding plural of said elements or steps, unless such exclusion is explicitly stated. For example, the phrase "a processor" may include a single processor, a multi-core processor, or a plurality of processors. If a plurality of processors are used, the plurality of processors may be found within a single unit (e.g., computer) or may be distributed throughout a system, such as in multiple units. If one processor is used, the claims may recite the processor as "only a single processor."

Furthermore, references to "one embodiment" are not intended to be interpreted as excluding the existence of additional embodiments that also incorporate the recited features. Moreover, unless explicitly stated to the contrary, embodiments that "comprise," "have," or "include" an element or a plurality of elements that have a particular property may also include additional such elements that do not have that particular property. Furthermore, when an element is described as being based on a factor or parameter, the term "based on" should not be interpreted as the factor or parameter being the sole factor or parameter, but may include the possibility that the element is also based on other factors or parameters.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., modules, processors, or memories) may be implemented in a single piece of hardware (e.g., a general purpose signal processor or random access memory, hard disk, or the like). Similarly, programs may be stand alone programs, may be incorporated as subroutines in an operating system, may be functions in an installed software package, may be a software surface package that is run from a computer server remotely, and the like. It should be understood that the various embodiments are not limited to the arrangements and instrumentality shown in the drawings.

FIG. 1 is a block diagram illustrating a system 100 formed in accordance with embodiments herein. The system 100 includes one or more client computing devices 110 that are capable of communicating over a network 112 with a server system 130. The server system 130 may include one or more web servers and, optionally, one or more application servers. The server system 130 may host a web application and have the tools, application program interfaces (APIs), and scripts, among other things, that may be used for the web application. In some embodiments, a web application includes a web site or web page that allows a user to view waveform data. The server system 130 may be only a single server or include a plurality of different servers that communicate with one another and the client computing devices 110 over the network 112. The server system 130, in some embodiments, is configured to receive and interpret requests through the network 112 from the client computing devices 110 or, more specifically, from software applications 146 of the client computing devices 110. The server system 130 is also configured to respond to the requests and transmit data to the client computing devices 110 in a predetermined format (e.g., HTML format). In some cases, the server system 130 and the client computing devices 110 may form a cloud-type computing system (e.g., public cloud, private cloud, or hybrid cloud).

The network 112 represents any one or combination of multiple different types of networks, such as cable networks, the Internet, private intranets, local area networks, wide area networks, wireless networks, and the like. In particular embodiments, the network 112 is the network of a healthcare facility (e.g., hospital) that allows access to authorized users (e.g., doctors, nurses, technicians, and the like) for reviewing medical information.

The client computing devices 110 may be implemented as any number of types of computing devices. These devices may include, for instance, personal computers (PCs), tablet computers, notebook computers, laptop computers, smart phones, electronic book readers, and so forth. In particular embodiments, the client computing devices 110 may include portable or handheld devices, such as tablet computers, notebook computers, laptop computers, and smart phones (e.g., iPhones). A portable or handheld device is relatively lightweight (e.g., less than three kilograms) such that an average adult individual may hold and re-orient the device during the course of its intended operation. In particular embodiments, the portable or handheld device is less than two kilograms.

In the illustrated embodiment, the portable or handheld device is a tablet computer 160. A user may be able to orient the portable device in a first layout orientation (e.g., portrait or vertical orientation) and in a second layout orientation (e.g., landscape or horizontal orientation). Data displayed on the portable devices may include, among other things, waveform data. The data may be reconfigured (e.g., re-sized) after the orientation of the portable device has changed. In some embodiments, the computing devices may be used for personal use and for business purposes.

The portable devices may also be configured to operate application programs, such as web browsers, mobile applications, or other software programs, that are capable of retrieving waveform data and displaying the waveform data through a communication network. The application program may be, for example, a third-party program (e.g., Google Chrome), a third-party mobile application (which may or may not include the same functionalities as a conventional web browser), or an application program configured for the enterprise using the application program. For instance, the application program may be developed using WebView. The communication network may include a private network, public network, or both. Non-limiting examples of web browsers include, such as Microsoft's Internet Explorer, Google Chrome, Mozilla Firefox, Opera, and Apple's Safari. The application programs may also be similar to mobile applications (referred to as "apps"). Optionally, the application programs may be configured to work with sub-applications or scripts (e.g., plug-ins or extensions) that are executed from within the application program or in concert with the application program. The sub-application runs or is executed concurrently with the application program. Optionally, the sub-application may be stored within the client computing system and/or the server system.

Application programs are typically third-party software that retrieve, present, and communicate information through the network. Application programs are configured to communicate with the server system 130 over the network 112. The application programs may communicate using, for example, a known protocol (e.g., Hypertext Transfer Protocol (HTTP) or HTTP-secure (HTTPS)). More specifically, the application programs may send requests (e.g., HTTP requests) for information to any web-accessible internet address. The application programs may also display the information in accordance with a predetermined format (e.g., HTML format). The sub-applications may be launched from within the application program and, optionally, communicate with the server system 130 to retrieve information that may be displayed to the user through the application program. Embodiments set forth herein may be implemented, at least in part, using an application program, a sub-application associated with the application program, or other software program having computer executable code.

In some embodiments, the server system 130 is configured to present a site (e.g., a website) that is capable of handling requests from one or more users and transmitting, in response, various pages (e.g., web pages) that are rendered at the client computing devices 110. For instance, the site can be any type of site that allows a user to view waveform data and, optionally, supports user interaction. In another example, the server system 130 may provide applications or sub-applications for the client computing devices 110 to download, store, and run locally. The server system 130 may additionally or alternatively interact with the client computing devices 110 to provide content in other ways.

As one example, the server system 130 may present an institutional website that allows access to medical data for a user that is authorized to view the medical data. The server system 130 may include, among other things, a content provider module 138, a session manager module 140, and an account manager module 142. The modules 138, 140 and 142, as well as other modules or services described herein, may be implemented by one or more processors performing program instructions to perform the operations described herein. The program instructions may be stored in data stores 134 or 136. The server system 130 interacts with one or more memories or data stores 134 and 136 in various manners as explained herein. One or both of the memories or data stores 134 and 136 may store program instructions to direct one or more processors to carry out the instructions described herein.

The data stores 134, 136 (as well as memory at the client computing devices 110) may also store various information, such as account-specific information about users of the site. The data store 134 may also store one or more catalogs related to items that may be viewed by the user. For example, web content (text, videos, pictures, and other content) may be stored therein. Content may also include electronic chart files 150 (e.g., health-monitoring charts) having waveform data as described below. The data associated with different web content may be transmitted to client computing devices 110 in response to individual client request designating location of such web content. It is recognized that the various content may be stored at locations distributed between various data storage areas, geographic locations, file structures, recommendation services, e-commerce catalogs and the like.

During operation, the session manager module 140 maintains network sessions with various client computing devices 110. The session manager module 140 responds to requests from the client computing devices 110 by providing authenticated and unauthenticated network resources. The session manager module 140 reviews incoming requests and determines whether the incoming requests seek access to authenticated or unauthenticated network resources. Requests for an authenticated network resource involve (e.g., require) privilege authentication before the session manager module 140 responds by granting access to the authenticated network resource. When privilege authentication is warranted/needed, the account manager module 142, returns an account lookup response including a prompt for non-sign-in credentials. The non-sign-in credentials corresponding to a type of content maintained in connection with user accounts. The non-sign-in credentials represent user specific information that is unique to a user and is not used as sign-in credentials for a corresponding network service. Optionally, the account manager module 142 may return an account authentication page including at least one of i) a sign-in credential fields or ii) a create new account option. Based on the user's entries at the account authentication page (as explained herein), the account manager module 142 the presents an account lookup response (e.g., when incorrect sign-in credentials are entered). The account manager module 142 may authorize the user to view the medical data, such as the waveform data described herein.

Also shown in FIG. 1, the tablet computer 160 includes a user display 122, which may be a touchscreen in some embodiments that is configured to identify and locate a touch from a user's finger or stylus. The user display 122 is framed by a housing 125 of the tablet computer 160. The user display 122 defines an area that may present virtual user-selectable elements 123 that may be selected by the user on the user display 122. Alternatively or in addition to the user-selectable elements 123, a user may select tangible or physical user-selectable elements 124 (e.g., buttons, switches, and the like).

Also shown in FIG. 1, the tablet computer 160 may include one or more processors 126, computer-readable storage media 127, a touch controller 128, and a gesture recognizer 131. The touch controller 128 is configured to detect touch events and communicate the touch events to the gesture recognizer 131. The gesture recognizer 131 may identify the input gesture based on the touch events and communicate the input gesture to one or more applications implemented by the device. Alternatively, the gesture recognizer may part of the application implemented by the device.

The computer-readable storage media 127 may store program instructions or computer code for the applications. For example, a display application 146 is configured to display a health-monitoring chart 129 on the user display 122. The display application 146 is configured to receive input gestures from a gesture recognizer of the device. In some embodiments, the computer-readable storage media 127 may store program instructions or computer code for a sub-application 148. Optionally, the sub-application 148 may be a plug-in or extension that is executable within or by the display application 146.

In some embodiments, the system 100 may include a monitoring system 154 that is communicatively coupled to detection devices (e.g., sensors or detectors) 156 that are configured to detect measurements, such as from an individual (e.g., a patient), and communicate the measurements to the system 154. The detection devices 156 may be configured to detect different physiological measurements, such as a heart rate, body temperature, blood pressure, respiratory rate, electrical activity, or intrauterine pressure. Non-limiting examples of a detection device include an electrode (e.g., ECG lead), a pulse oximeter, a heart rate monitor, a detector that monitors motion of the patient (e.g., accelerometer or global positioning system (GPS) device), a non-invasive blood pressure (NIBP) monitor (e.g., NIBP cuff), a respiratory monitor, and the like. The monitoring system 154 may communicate data to the server system 130 that is based on the detected physiological measurements.

The modules 123-125 (and the system controller 114) include one or more processors. A processor may include a microprocessor or other logic-based device. The processor may be or be part of a controller or microcontrollers. A processor operates based on instructions stored on a tangible and non-transitory computer readable storage medium. A processor may operate based on hardwired instructions. The databases 130 and 132 can be or include electrically erasable programmable read only memory (EEPROM), simple read only memory (ROM), programmable read only memory (PROM), erasable programmable read only memory (EPROM), FLASH memory, a hard drive, or other type of computer memory.

As used herein, the terms "computer" or "computing system" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer" or "computing system."

The computer or processor executes a set of instructions that are stored in one or more storage elements, in order to process input data and provide output data in the form of a health-monitoring chart, among other things. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes described herein. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine. The program is compiled to run on designated operating systems.

Figure 2:
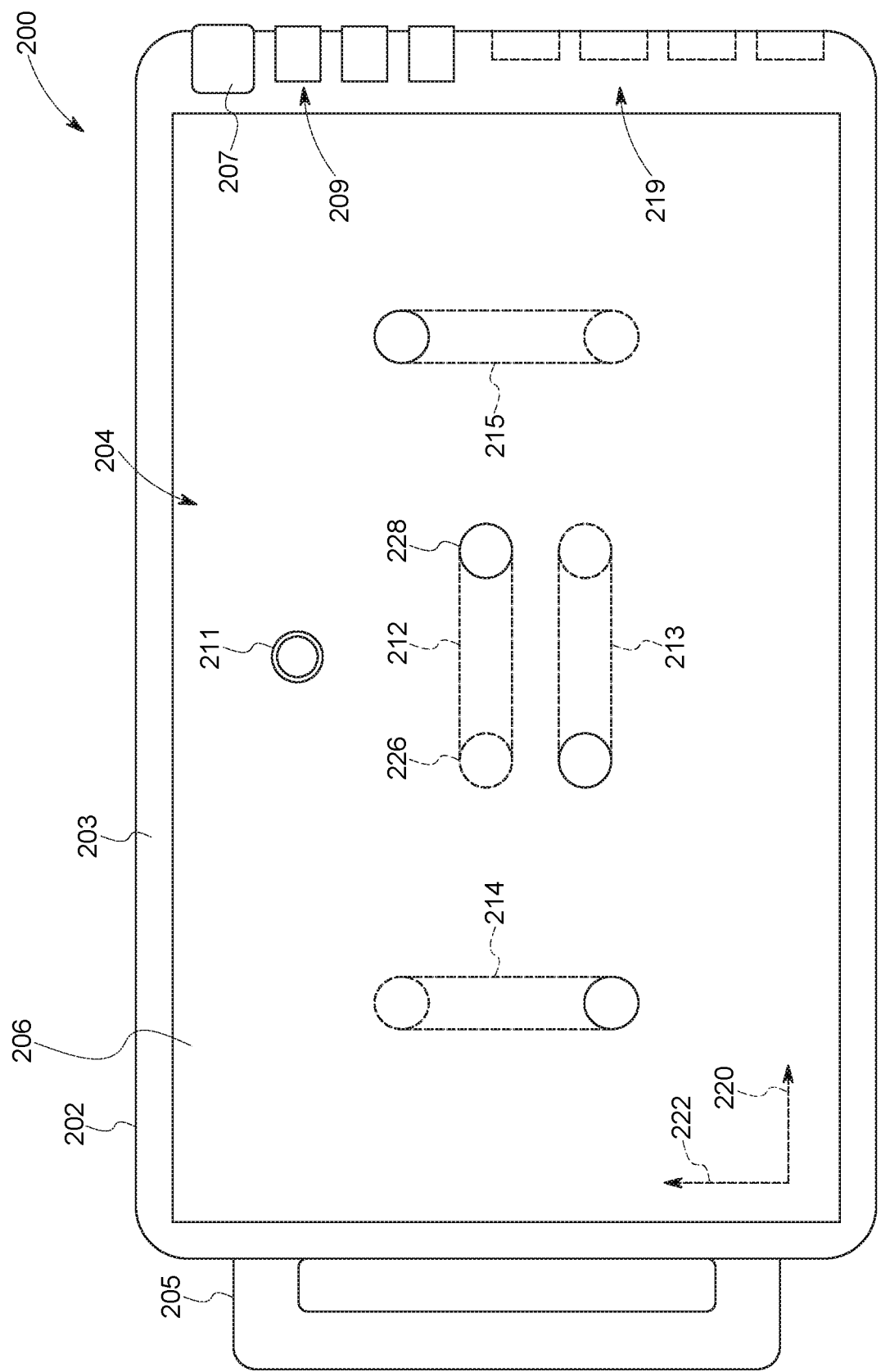
FIG. 2 illustrates a patient-monitoring device in accordance with an embodiment and examples of input gestures that may be detected by a touchscreen of the patient-monitoring device.

FIG. 2 illustrates a patient-monitoring device 200 in accordance with an embodiment. The patient-monitoring device 200 is configured to display information to a healthcare provider on a display area 206 for assessing the health of the patient. The display area 206 is blank in FIG. 2. Examples of information that may be viewed in the display area 206 are shown in FIGS. 3-12.

The patient-monitoring device 200 may be a handheld device. In some embodiments, the patient-monitoring device is a proprietary device having custom-designed circuitry, firmware, and/or software configured to carry out one or more of the methods set forth herein. In other embodiments, the patient-monitoring device 550 is an off-the-shelf computing device, such as a tablet computer or smartphone, that has an application program installed for carrying out one or more of the methods set forth herein. For example, the patient-monitoring device 550 may be the user's personal smartphone or tablet computer having the application program for monitoring the patient installed, among other application programs.

The patient-monitoring device 200 includes, among other things, a device body or housing 202 and a touchscreen 204 that is exposed for user interactions (e.g., viewing and touching). The device body 202 includes a frame 203 that surrounds a perimeter of the touchscreen 204 and an operator handle 205 that is configured to be gripped by the user. Also shown, the patient-monitoring device 200 has physical or tangible user-selectable elements 207, 209 and a plurality of ports 219 (e.g., electrical and/or optical connectors). The user-selectable element 207 may be, for example, a power button. The user-selectable elements 209 may provide other functionalities. The ports 219 open along a side edge of the device body 202 and are configured to mate with respective plugs from other devices, such as the detection devices described herein. The patient-monitoring device 200 also includes internal circuitry, such as the various elements described with respect to the patient monitoring device 550 in FIG. 14.

The touchscreen 204 has the display area 206, which may or may not cover the entire touchscreen. The touchscreen 204 is configured to detect a touch event from a user's body (e.g., finger) or stylus on the display area 206, identify the location where the touch event occurred along the display area 206, and communicate the touch event. The touch-sensing technology may be, for example, based on a change in capacitance or piezoelectricity along the display area. Other touch-sensing technologies exist (e.g., optical imaging, dispersive signal, acoustic pulse recognition) and may be suitable for embodiments set forth herein.

The display area 206 is configured to present graphical representations to the user, such as those provided by an application. The display area 206 is oriented with respect to a horizontal axis 220 and a vertical axis 222. As shown, the horizontal axis 220 extends along the greatest dimension of the patient-monitoring device 200, and the vertical axis 222 extends along a different dimension of the patient-monitoring device 200. In other embodiments, such as those shown in FIGS. 11 and 12, the vertical axis may extend along the greatest dimension of the patient-monitoring device 200.

A number of input gestures are illustrated along the display area 206. The input gestures include a tap 211, which may or may not include multiple taps in quick succession. The input gestures also include a horizontal swipe in a first direction (identified as 212), a horizontal swipe in an opposite direction (identified as 213), a vertical swipe in a first direction (identified as 214), a vertical swipe in an opposite direction (identified as 215). It is also contemplated that the input gestures may include swipes in other directions. Swipes extend for at least a predetermined distance. In FIG. 2, the dashed circles 226 represent the location of the initial touch, and the solid filled circles 228 represent where the touch event ends, such as when the user's finger is removed. The distance between the circles 226 and 228 is at least the predetermined distance.

Also shown in FIG. 2, the display area 206 may show section identifiers 231, 232. In the illustrated embodiment, the section identifiers 231, 232 are dots or small circles that indicate a (a) number of sections that are viewable and (b) and order of sections. For example, the section identifiers include only two identifiers, thereby indicating that the health-monitoring chart has two different sections that show the parameters. Moreover, the section identifier 231 is filled, thereby indicating that the section presently shown is the first of two sections and the section that is not presently shown is the second section. In other embodiments, the section identifiers may be numbers that indicate the total number of sections and the present section shown. For example, the section identifier may be "2/5", which indicates that the presently shown section is the second section and the chart includes a total of five sections that show parameters. The sections may also be referred to as pages or sheets.

Figure 3:
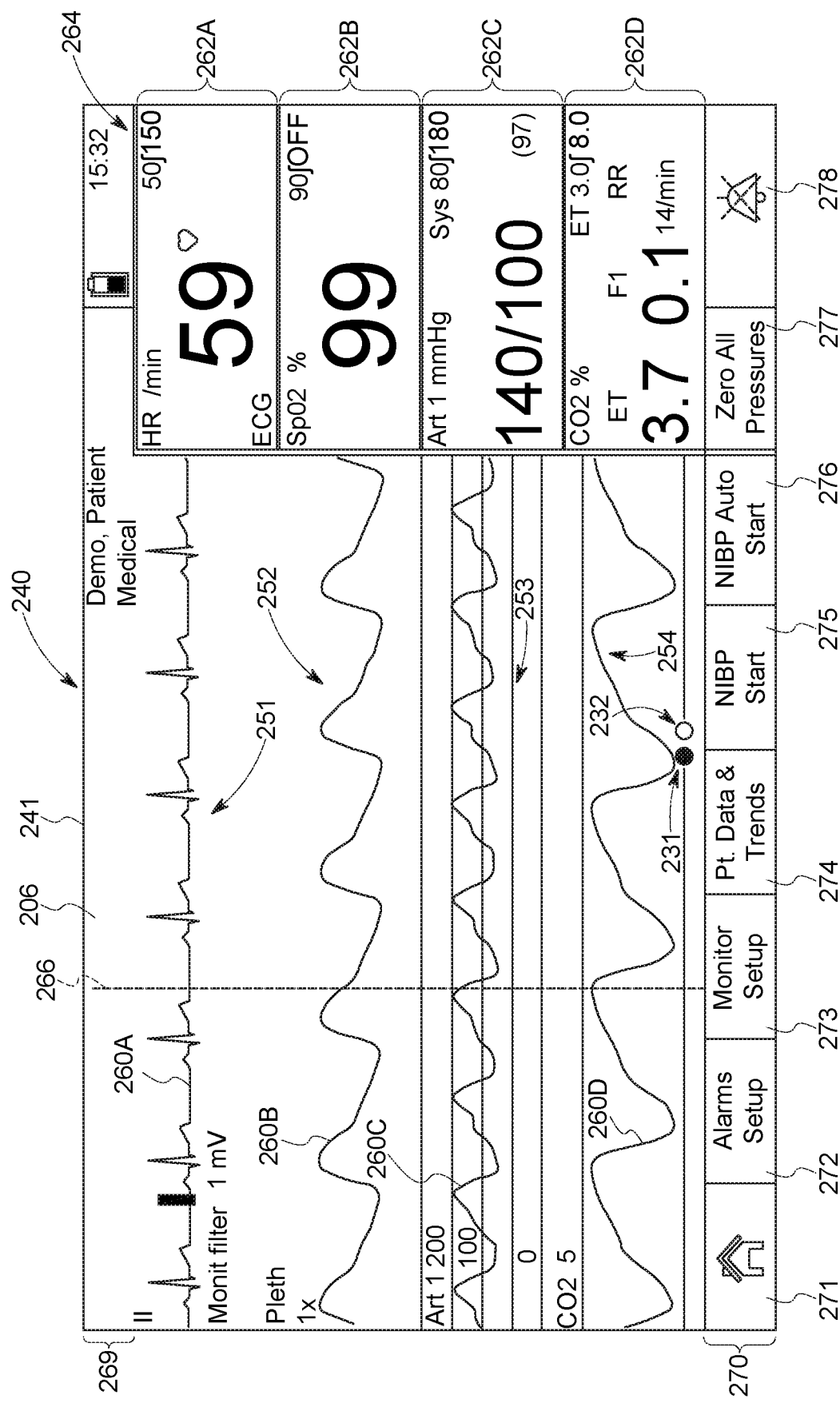
FIG. 3 illustrates a first chart section of a health-monitoring chart that may be presented to a user of the patient-monitoring device of FIG. 2.

FIG. 3 illustrates a first chart section 241 of a health-monitoring chart 240 that may be presented to a user of the patient-monitoring device 200. The first chart section 241 includes parameter regions 251-254. The health-monitoring chart 240 includes a second chart section 242 (shown in FIG. 4), which includes parameter regions 255-258 (shown in FIG. 4). Returning to FIG. 3, the parameter regions 251-254 are positioned relative to one another. The parameter regions 251-254 are rectangular areas or strips that extend at least partially across the display area 206. The parameter regions may be positioned in accordance with a predetermined standard for assessing a condition. In other embodiments, the user may select the positions of the parameter regions.

Each of the parameter regions 251-254 is based on a respective patient parameter and includes a parameter signal line 260 and a value area 262 that is aligned with the parameter signal line 260. The value area 262 also indicates limit information 264 for the respective patient parameter. In the illustrated embodiment, the parameter region 251 includes a parameter signal line 260A and a value area 262A that correspond to a heart rate (heart rates per minute) based on ECG data. The limit information 264 indicates that the upper limit for the heart rate is 150 and the lower limit for the heart rate is 50. The parameter region 252 includes a parameter signal line 260B and a value area 262B that correspond to a $SpO_2$. The limit information 264 indicates that the lower limit for the $SpO_2$ is 90 and no upper limit exists. The parameter region 253 includes a parameter signal line 260C and a value area 262C that correspond to an arterial systolic pressure. The limit information 264 indicates that the lower limit for the pressure is 80 and the upper limit for the pressure is 180. The parameter region 254 includes a parameter signal line 260D and a value area 262D that correspond to an estimate of carbon dioxide (% $CO_2$) in the blood. The limit information 264 indicates that the lower limit for the pressure is 3.0% and the upper limit for the pressure is 8.0%.

Optionally, the positions of the parameter regions 251-254 may be consistent with established standards for the conditions sought to be diagnosed. By way of example, the parameter regions 251-254 are vertically stacked (or stacked along the vertical axis) and the parameter signal lines 260 of the parameter regions 251-254 are essentially synchronized. As such, the values of the patient parameters that intersect a common vertical line 266 (dashed line) represent the values of the different patient parameters that occur at essentially the same time. The vertical line 266 may or may not be visible to the user.

Also shown, the display area 206 illustrates a user-control region 270 and a status region 269. The status region 269 includes information for identifying the patient and information regarding a power status of the device 200. The user-control region 270 includes virtual user-selectable elements 271-278. In response to an input gesture that selects the user-selectable element 271 was selected, the application returns the application to a home screen (not shown). In response to an input gesture that selects the user-selectable element 272 was selected, the application presents an alarms setup section in which the user may select the predetermined conditions by which the patient parameters are compared. In response to an input gesture that selects the user-selectable element 273 was selected, the application presents a monitor setup section in which the user may select options for displaying the patient parameters (e.g., positions of the parameter regions).

Figure 4:
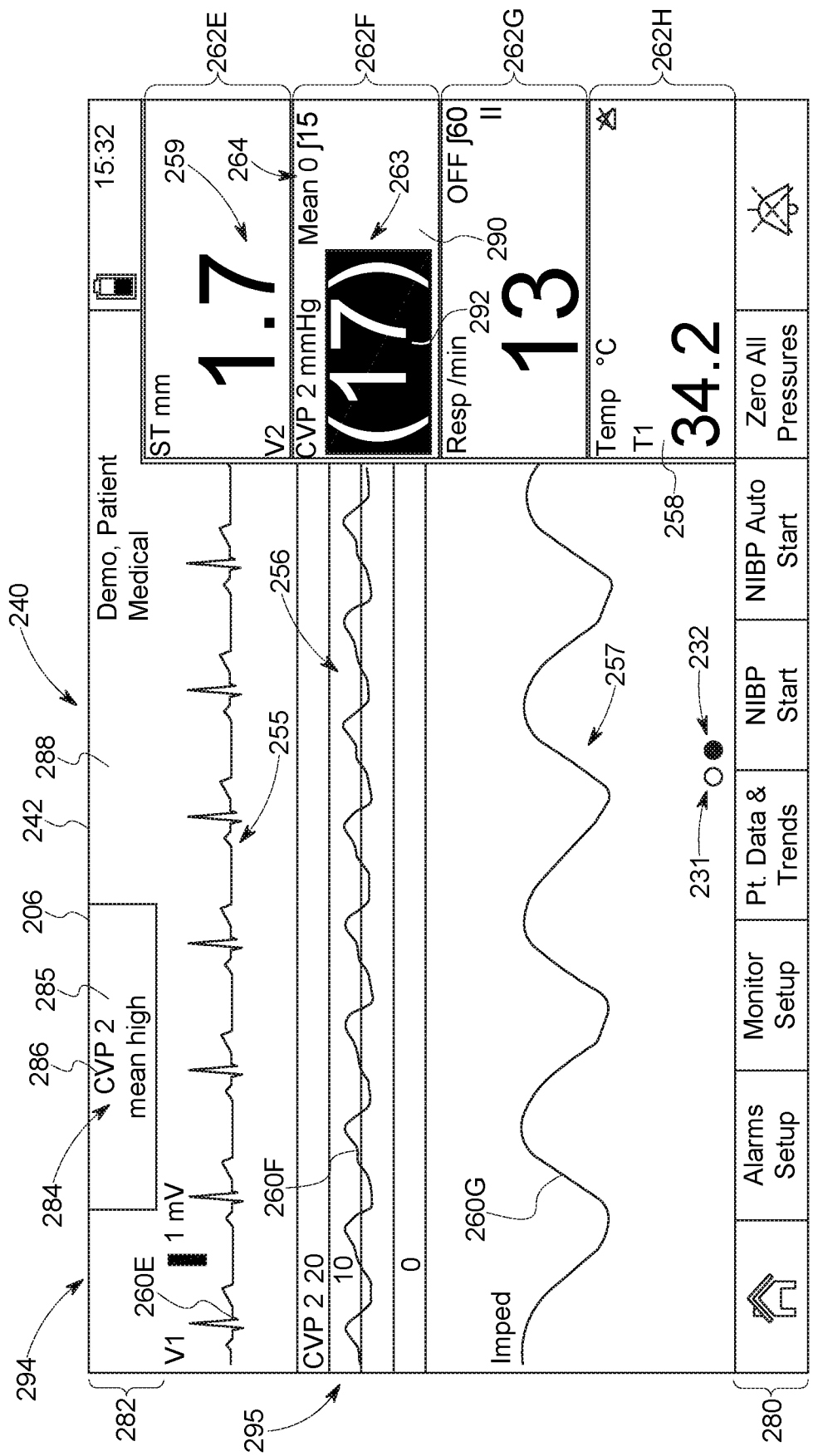
FIG. 4 illustrates a second chart section of the health-monitoring chart that may be presented to the user of the patient-monitoring device of FIG. 2.

FIG. 4 illustrates the second chart section 242 of the health-monitoring chart 240 shown in the display area 206 of the patient-monitoring device 200. The second chart section 242 includes parameter regions 255-259, which may include similar features as the parameter regions 251-254

(FIG. 3). For example, the parameter regions 255-259 are rectangular areas that extend at least partially across the display area 206. The parameter regions may be positioned in accordance with a predetermined standard for assessing a condition. In other embodiments, the user may select the positions of the parameter regions.

Each of the parameter regions 256 and 257 is based on a respective patient parameter and includes a parameter signal line 260 and a value area 262 that is aligned with the parameter signal line 260. More specifically, the patient parameter of the parameter region 256 is a central venous pressure (CVP), and the parameter region 256 includes a parameter signal line 260F and a value area 262F. The patient parameter of the parameter region 257 is a respiration rate, and the parameter region 257 includes a parameter signal line 260G, which indicates impedance, and a value area 262G, which provides a number of respirations per minute.

The parameter region 255 includes only a parameter signal line 260E. The parameter region 259 includes only a value area 262E, and the parameter region 258 includes only a value area 262H. The patient parameters for the parameter regions 255, 259 are based on ECG data. The patient parameters for the parameter regions 255, 259 are based on ECG data. The patient parameters for the parameter regions 255, 259 are voltages corresponding to the precordial leads V1, V2, respectively. The patient parameter of the parameter region 258 is a body temperature. For some patient parameters, the value area 262 indicates limit information 264 for the respective patient parameter.

Optionally, the positions of the parameter regions 255-259 may be consistent with established standards for the conditions sought to be diagnosed. By way of example, the parameter regions 255-257 are vertically stacked (or stacked along the vertical axis) and the parameter signal lines 260 of the parameter regions 255-257 are essentially synchronized.

Also shown, the second chart section 242 includes a user-control region 280 and a status region 282. In some embodiments, the user-control region 280 is identical to the user-control region 270 and includes the same user-selectable elements 271-278. In other embodiments, the user-control region 280 and the user-control region 270 may not have the same set of user-selectable elements. In some embodiments, the status region 282 is identical to the status region 269.

The second chart section 242 also includes a parameter alert or notice 284. The parameter alert 284 may issue in response to determining that a patient parameter is significant. As such, the parameter alert 284 does not appear in the second chart section 242 when the patient parameters are not determined to be significant. The parameter alert 284 has a designated shape and background color 285. Optionally, the parameter alert 284 may include textural information 286 that identifies which patient parameter has been determined to be significant. The textural information 286 may provide additional information. The textural information 286 in FIG. 4 is "CVP 2 Mean High." As such, the textual information 286 identifies the patient parameter and a reason why the patient parameter is significant.

The background color 285 differs from a background color 288 of the surrounding portion of the second chart section 242. For example, the background color 288 may be black and the background color 285 may be yellow, red, blue, or green. In some embodiments, the background color 285 is a function of the patient parameter that has been determined to be significant. For example, the parameter alert for a first patient parameter may be yellow, the parameter alert for a second patient parameter may be green, and the parameter alert for a third patient parameter may be blue.

As shown, the parameter alert 284 is located along a top edge 294 of the display area 206 and closer to a left edge 294 of the display area 206. The parameter alert 284 is disposed in the status region 282. The parameter alert 284 may appear in an area that does not does have other information. For example, the parameter alert 206 does not appear to cover a parameter signal line or a parameter value. In other embodiments, however, the parameter alert may cover other information.

When a patient parameter has been determined to be significant, at least a portion of the parameter region that corresponds to the patient parameter may also indicate that the patient parameter is significant. For example, in FIG. 4, the value area 262F includes a number 263 representing a value of the patient parameter and a background color 290. During an alert, at least a portion of the background may have a different background color 292. For example, the background color 290 may be black, and the background color 292 may be yellow, red, blue, or green. The background color 292 may be the same as the background color 285.

In some embodiments, the first chart section 241, the second chart section 242, and any optional other chart sections are predetermined chart sections. Such chart sections have a predetermined arrangement of parameter regions that were determined by the device, user, or system. Optionally, the second chart section 242 may be a condition-specific chart section as described herein.

Figure 5:
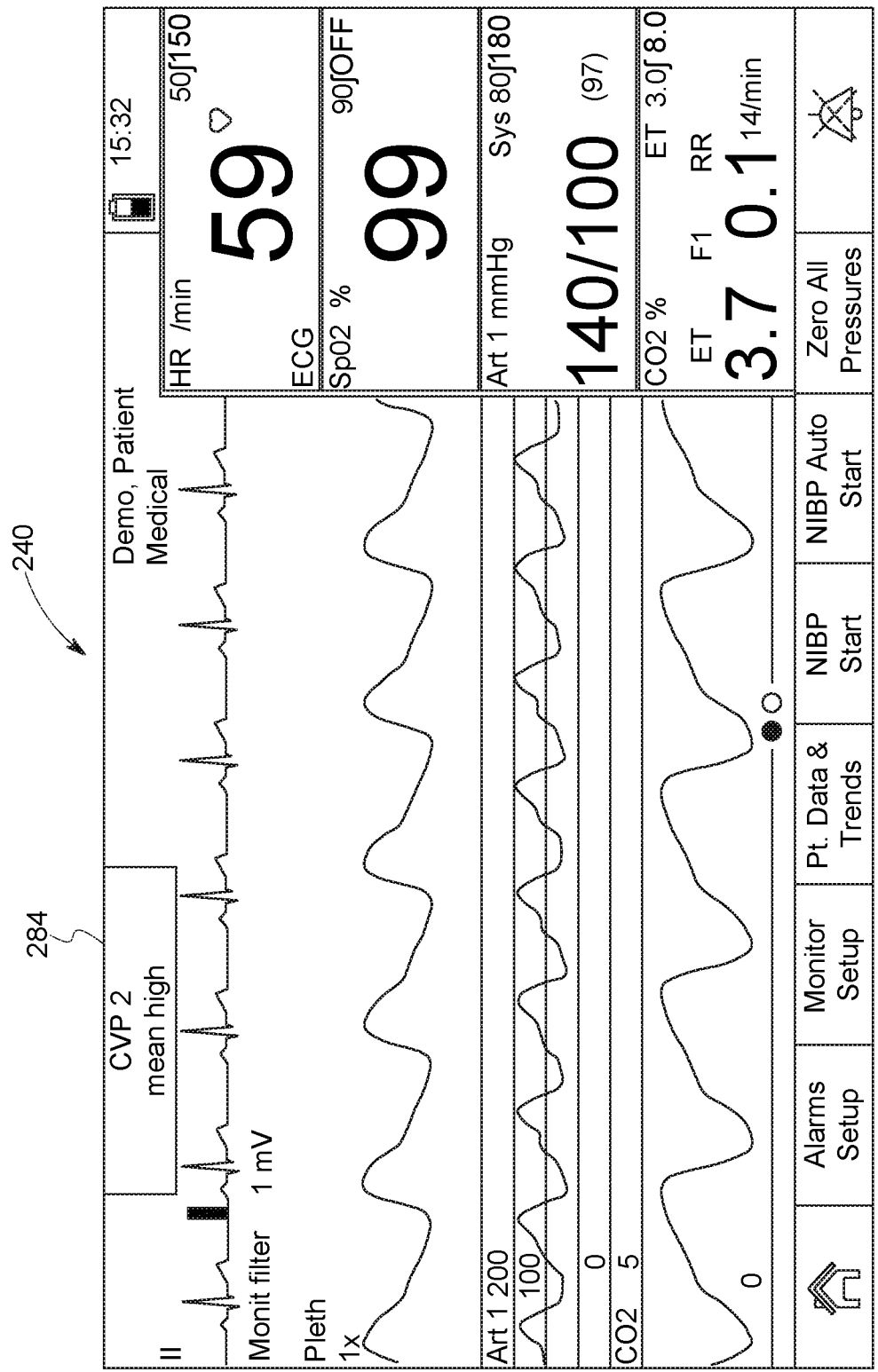
FIG. 5 illustrates the first chart section of the health-monitoring chart including a parameter alert relating to a patient parameter that is not shown in the first chart section.

FIG. 5 illustrates the first chart section 241 of the health-monitoring chart 240 when a parameter alert is issued. As shown, the first chart section 240 is presented to the user on the touchscreen 204 while the second chart section 242 (FIG. 4) is not presented on the touchscreen 204. The parameter alert 284 is shown in the first chart section 241, despite the parameter alert 284 corresponding to a patient parameter that is not shown in the first chart section 241. The parameter alert 284 may have a similar position or an identical position compared to the position of the parameter alert 284 in the second chart section 242 (FIG. 4). In addition to the parameter alert 284, the device 200 may issue an audible noise (e.g., series of beeps) and/or a tactile notification (e.g., vibration) in response to determining that a patient parameter is significant.

Figure 6:
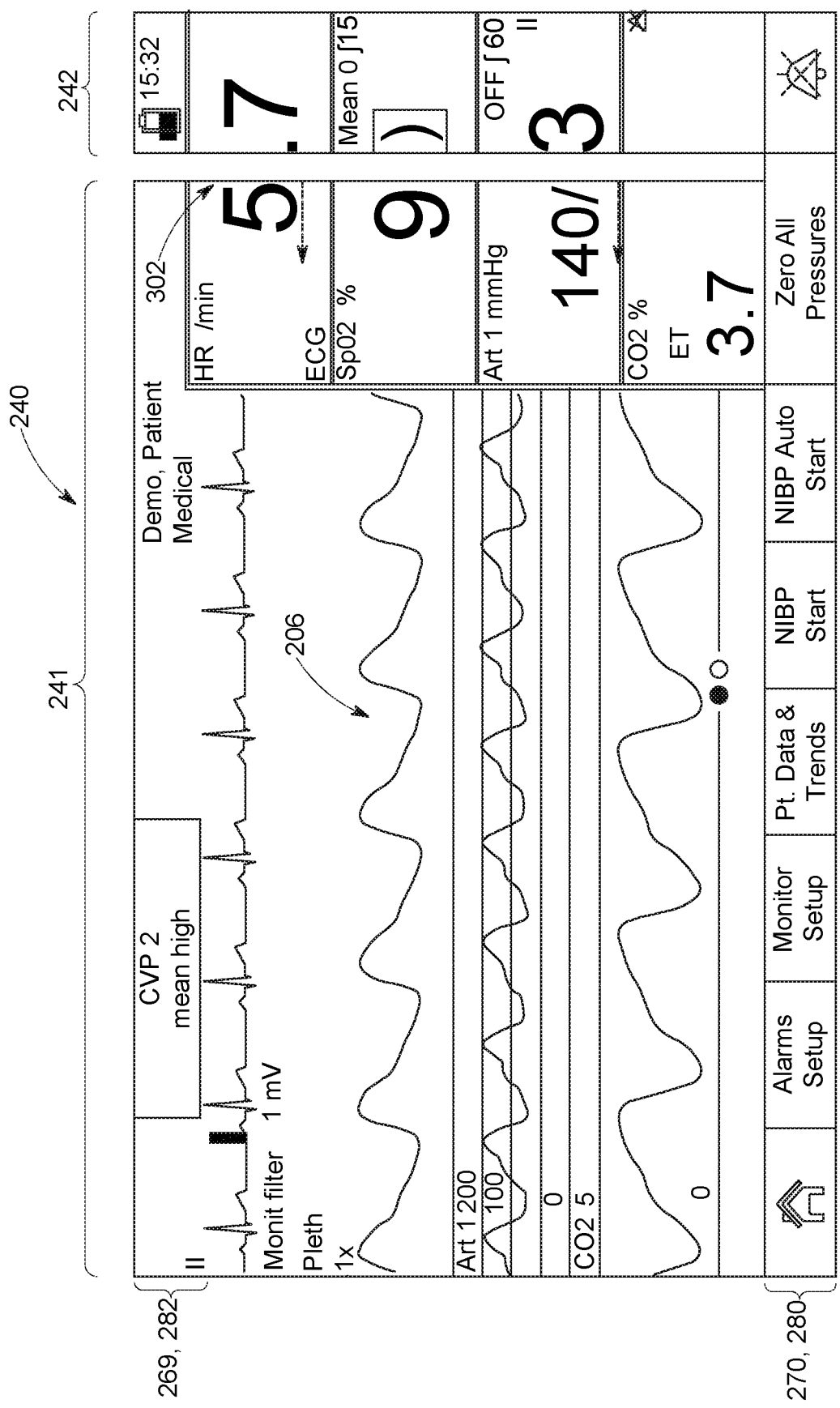
FIG. 6 illustrates the health-monitoring chart transitioning from the first chart section to the second chart section at a first stage in accordance with an embodiment.
Figure 7:
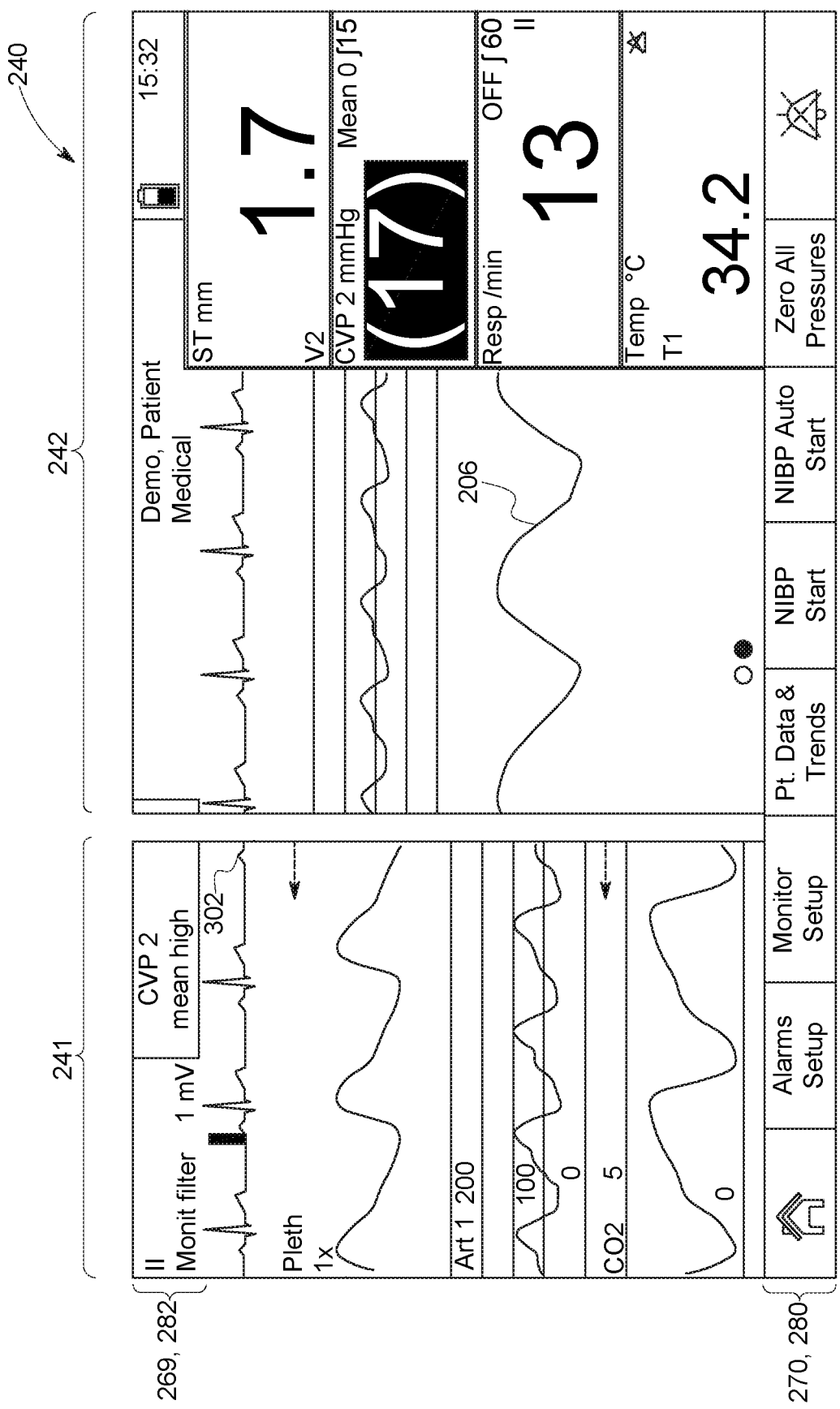
FIG. 7 illustrates the health-monitoring chart in FIG. 6 transitioning from the first chart section to the second chart section at a second stage in accordance with an embodiment.

FIGS. 6 and 7 illustrate the health-monitoring chart 240 as the health-monitoring chart 240 transitions from the first chart section 241 to the second chart section 242 in accordance with an embodiment. It should be understood that the following description of transitions from the first chart section 241 to the second chart section 242 may also be applied to transitions from the second chart section 242 to the first chart section 241.

In some embodiments, the application may automatically transition, in response to determining that a patient parameter has become significant, from one chart section that is displayed to the other chart section. In other embodiments, however, the transition may occur in response to detecting an input gesture on the touchscreen 204. For example, the input gesture may be indicative of a swipe along the touchscreen 204 or a tap (or double-tap) on the touchscreen 204. A swipe input gesture may extend generally in a swipe direction for at least a predetermined distance along the touchscreen 204.

In FIGS. 6 and 7, the application is transitioning from the first chart section 241 to the second chart section 242. In the transition, the first chart section 241 appears to be progressively cropped (or removed) as if wiped from one edge to the opposite edge while the second chart section 242 appears to replace a void left by the first chart section 241. This type of transition may be referred to as a wipe transition in which one chart section progressively disappears while the other chart section progressively appears.

A solid line 302 indicates a cut-off boundary where the first chart section 241 ends and the second chart section 242 appears. The solid line 302 may or may not appear during the transition. During the transition, portions of the display area 206 may appear unchanged. For example, the status regions and the user-control regions may be identical and, as such, the display does not change as the cut-off boundary moves across the display area 206.

In some embodiments, an audible sound and/or a tactile event may occur concurrently with the transition to notify the user that a transition has occurred. For example, the audible sound may resemble the sound of a page in a book turning. The tactile event may be vibration.

Figure 8:
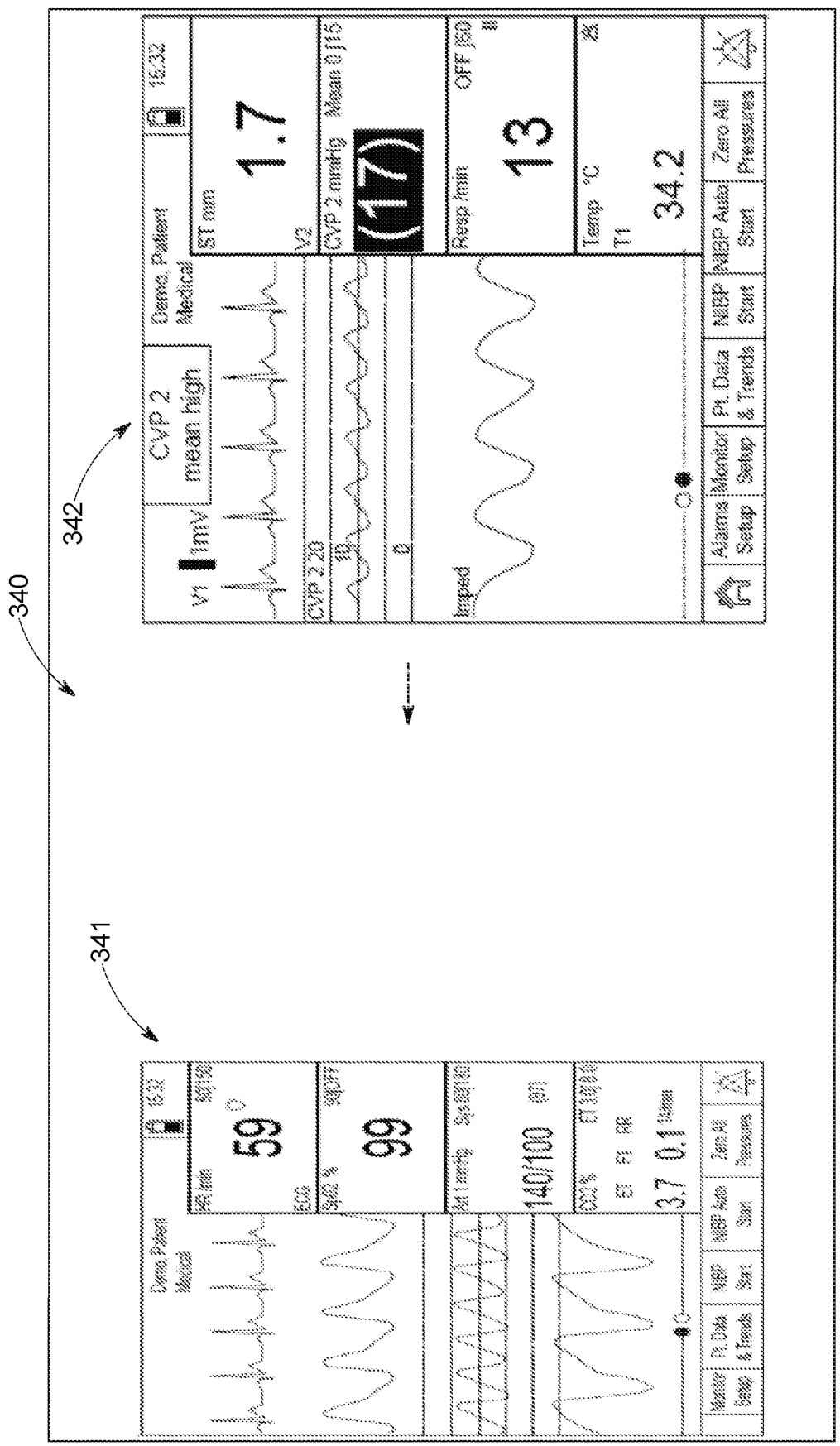
FIG. 8 illustrates the health-monitoring chart transitioning from the first chart section to the second chart section in accordance with an embodiment.

FIG. 8 illustrates a health-monitoring chart 340 as the health-monitoring chart 340 transitions from a first chart section 341 to a second chart section 342. The health-monitoring chart 340 may be similar or identical to the health-monitoring chart 240 (FIG. 3), and the first and second chart sections 341, 342 may be similar or identical to the first and second chart sections 241, 242, respectively (FIGS. 3 and 4 respectively).

The first chart section and the second chart section may be separate and discrete sections. For example, the parameter regions of the first and second chart sections may not be shared by the same page such that the user may vertically scroll from the parameter regions of the first chart section to the parameter regions of the second chart section.

In some embodiments, a current (or displayed) chart section may be instantly replaced by another chart section without the appearance of vertical or horizontal movement from one chart section to the next chart section. In other embodiments, however, a transition from one chart section to another chart section may be shown. For example, the transition may include moving one chart section, as a discrete section, away from the display area while another chart section is moved toward the display area. It should be understood that "moving" a chart section with respect to a display area includes the appearance of moving the chart section relative to the display area. The chart sections may appear as discrete sections such that the parameter regions, including any parameter signal lines or value areas, have fixed positions relative to one another during the transition.

In FIG. 8, the first chart section 341 is moving away from the display area 206 while the second chart section 342 is moving toward the display area 206. More specifically, the second chart section 342 is moving to be positioned within the display area 206 such that the second chart section 342 may be viewed while the first chart section 341 is hidden. In FIG. 8, the first chart section 341 appears to have backed away from the display area 206 and is rotating away from the user. The second chart section 342 appears to have moved from off-screen and is rotating toward the user such that the second chart section 342 is presented to the user. As described herein, the transition shown in FIG. 8 may occur automatically, in response to determining that a patient parameter in the hidden chart section is significant, or may be initiated manually by an input gesture from the user.

Figure 9:
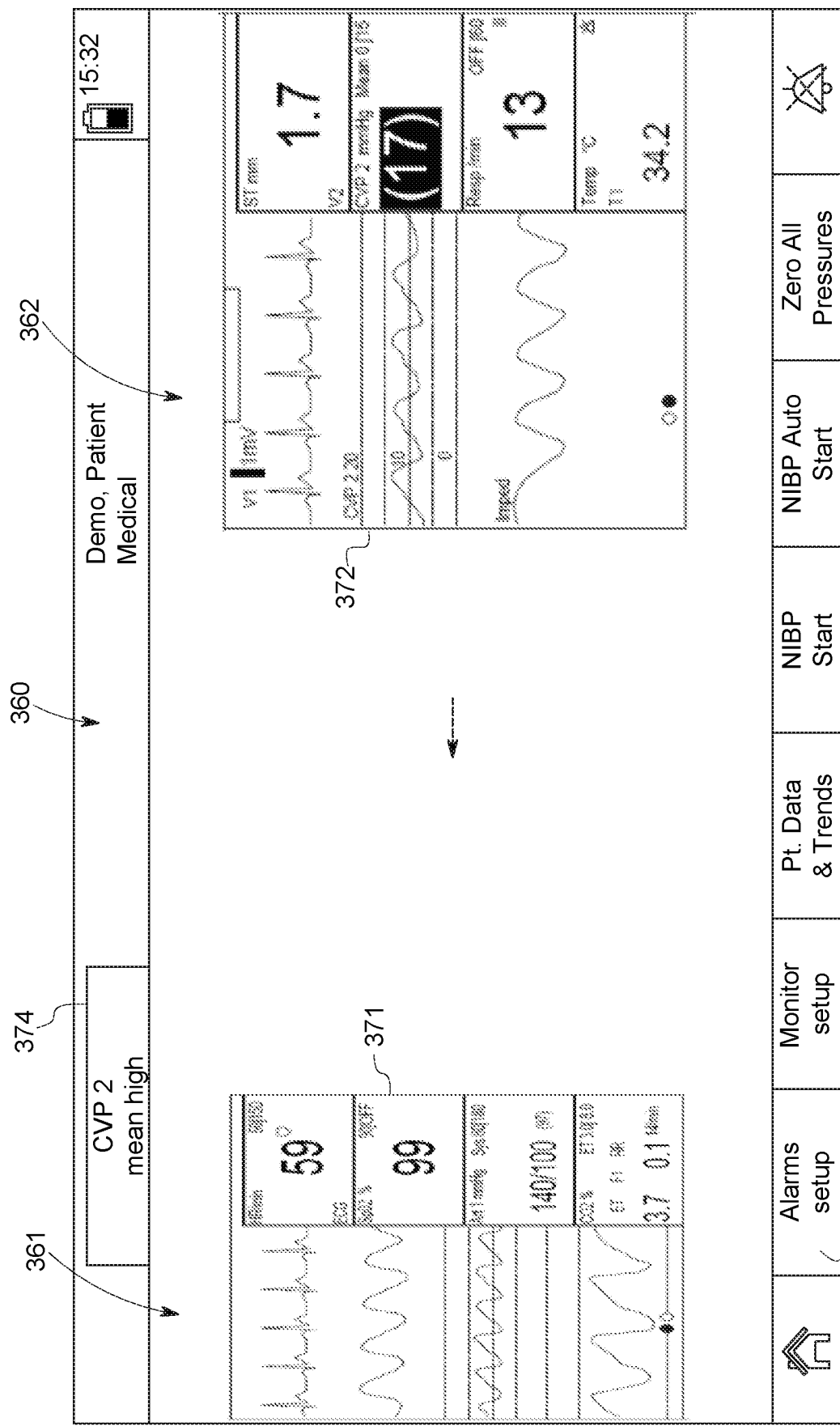
FIG. 9 illustrates the health-monitoring chart transitioning from the first chart section to the second chart section in accordance with an embodiment.

FIG. 9 illustrates a health-monitoring chart 360 as the health-monitoring chart 360 transitions from a first chart section 361 to a second chart section 362. The health-monitoring chart 360 may be similar or identical to the health-monitoring chart 240 (FIG. 3), and the first and second chart sections 361, 362 may be similar or identical to the first and second chart sections 241, 242, respectively (FIGS. 3 and 4 respectively).

The transition shown in FIG. 9 is similar to the transition shown in FIG. 8. However, the transition in FIG. 9 includes portions of the first chart section 361 remaining while active fields 371, 372 are transitioned. More specifically, a status region 374 and a user-control region 376 do not appear to move. In some embodiments, the status region 374 and the user-control region 376 do not appear to change. The active fields 371, 372 are discrete portions of the chart section that include the parameter regions. The parameter regions within each of the active fields have fixed positions with respect to one another. As such, the transition in FIG. 9 moves the parameter regions while appearing to allow other regions to remain stationary. Although the transition in FIG. 9 is similar to the transition in FIG. 8, other embodiments may include a transition that is similar to the transition shown in FIGS. 6 and 7 such that the active areas 371, 372 are the only portions of the chart sections that are wiped.

Figure 10:
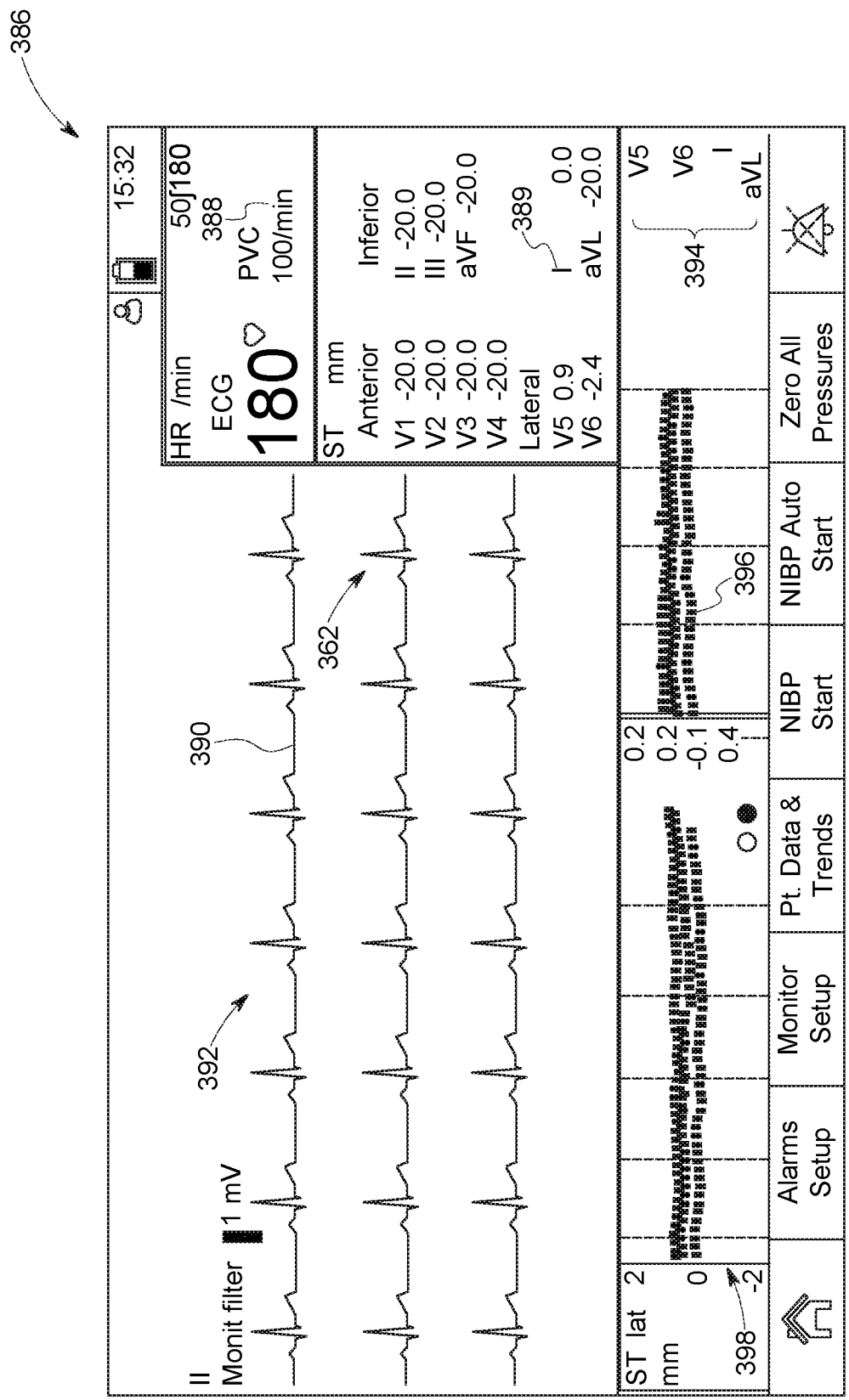
FIG. 10 illustrates a condition-specific chart section of the health-monitoring chart in accordance with an embodiment.

FIG. 10 illustrates a condition-specific chart section 386 that may be displayed to a user of the patient-monitoring device 200 (FIG. 2). Patient parameters may be associated with predetermined conditions. For example, an excessive value for a certain patient parameter may be associated with a predetermined condition, but a value that is too low for the patient parameter may be associated with a different predetermined condition. When determining whether the patient has a predetermined condition, a healthcare provider may desire to view additional patient parameters that can also be used to determine the predetermined condition. Accordingly, in response to determining that one patient parameter is significant, embodiments may generate a condition-specific chart section that is configured to provide more information and/or present information in a manner that is better for determining whether the patient has the predetermined condition. The condition-specific chart section may include a group of patient parameters that are configured for assessing the predetermined condition. The condition-specific chart section may provide more information related to the predetermined condition than shown in the first chart section and the second chart section.

The condition-specific chart section 386 shown in FIG. 10 may be generated after a patient parameter is determined to be significant. For example, the condition-specific chart section 386 may be generated in response to determining that the heart rate is significant. The condition-specific chart section 386 includes the heart rate (referenced at 388), which was determined to be significant, and additional information related to a cardiac condition. For example, the condition-specific chart section 386 includes values relating to ECG leads at a parameter region 389. In a 12-lead electrocardiogram, the patient parameters include the six chest leads that detect the depolarization wave in the frontal plane. These may also be referred to as the precordial leads and are V1, V2, V3, V4, V5, and V6. Each of the chest leads corresponds to an electrode that has a designated position on the patient's chest. The patient parameters also include extremity leads I, II, III, aVL, and aVF. The extremity leads are derived from electrodes that are positioned on the left and right arm and left and right legs.

Values for each of the precordial leads and each of the extremity leads are shown in the parameter region 389 in FIG. 10. In other embodiments, however, fewer of the leads may be shown. FIG. 10 also shows a signal line 390 of the extremity lead II at a parameter region 392. Also shown, trend lines 396 of leads V5, V6, I, and aVL are shown in a parameter region 398. The trend lines 396 may be color-coded to match a color of the labels 394 for leads V5, V6, I, and aVL.

Figure 11:
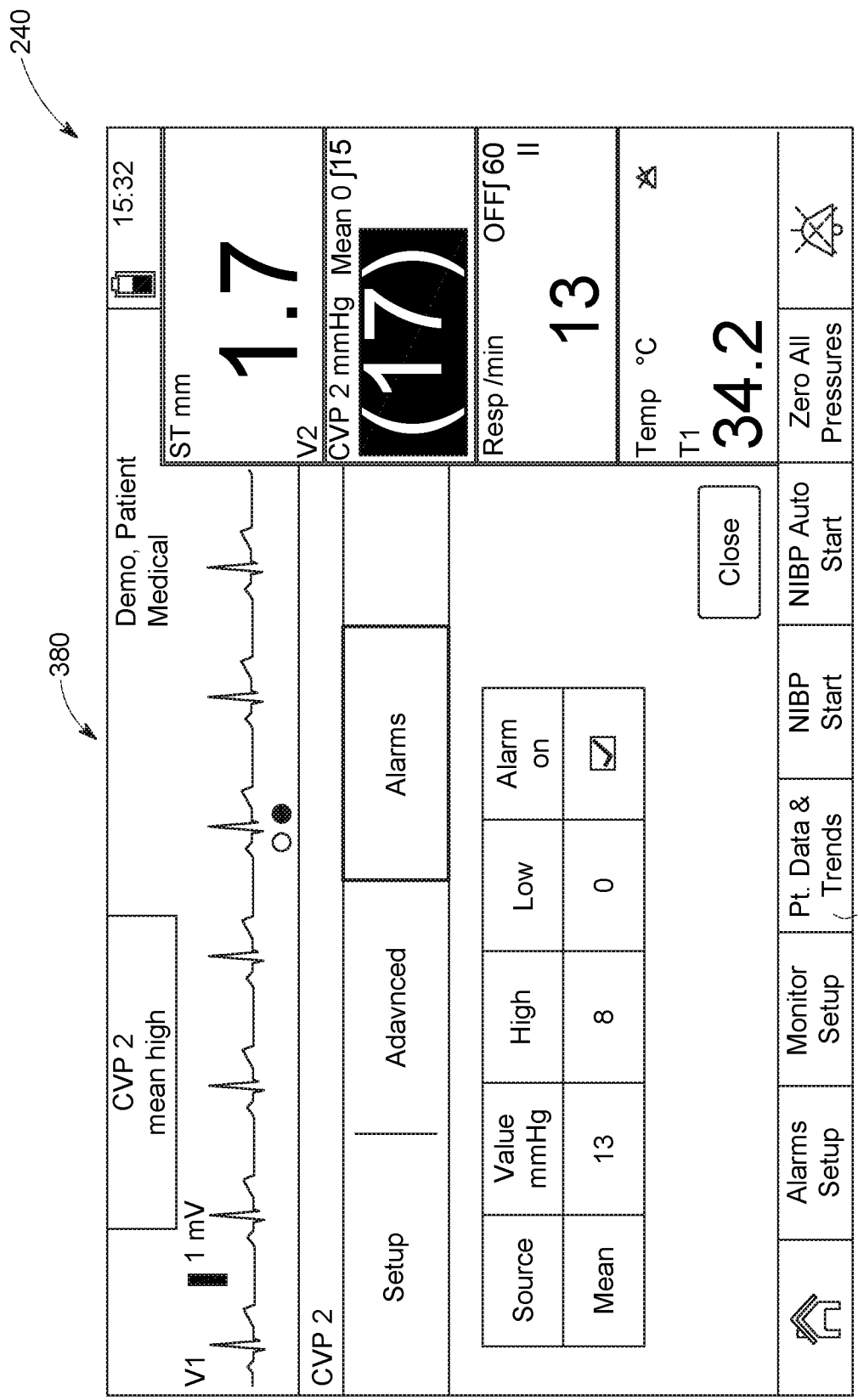
FIG. 11 illustrates a user-selection section of the health-monitoring chart in accordance with an embodiment.

FIG. 11 illustrates a user-selection section 380 of the health-monitoring chart 240 in accordance with an embodiment. The user-selection section 380 may appear in response to an input gesture being detected at the user-selectable element 274. The user-selection section 380 may enable the user to select patient parameters and/or change the designated conditions that are applied to the patient parameter. For example, a user may be able to change upper or lower limits that are applied to the CVP. In some embodiments, the chart sections may be manually configured by the user. In other embodiments, the chart sections may be automatically configured by the patient-monitoring device.

Returning briefly to FIGS. 3 and 4, in some embodiments, the positions of the parameter regions 251-259 may be selected or changed by the user of the device. A user may prefer a certain arrangement of the parameter regions 251-259 over other arrangements when assessing the health status. For example, the user may believe that he or she may more quickly recognize a pattern when the parameter regions 251-259 are arranged in a designated order. As such, embodiments may enable the user to move the parameter regions 251-259 relative to one another. For example, a user may select a parameter region and drag the parameter region to a different position (e.g., at a top position, bottom position, or in between two other graph regions). The system may automatically move the other parameter regions. In some embodiments, the user may select the patient parameters that are to be displayed on the first chart section, and the user may select the one or more patient parameters that are to be displayed on the first chart section.

Figure 12:
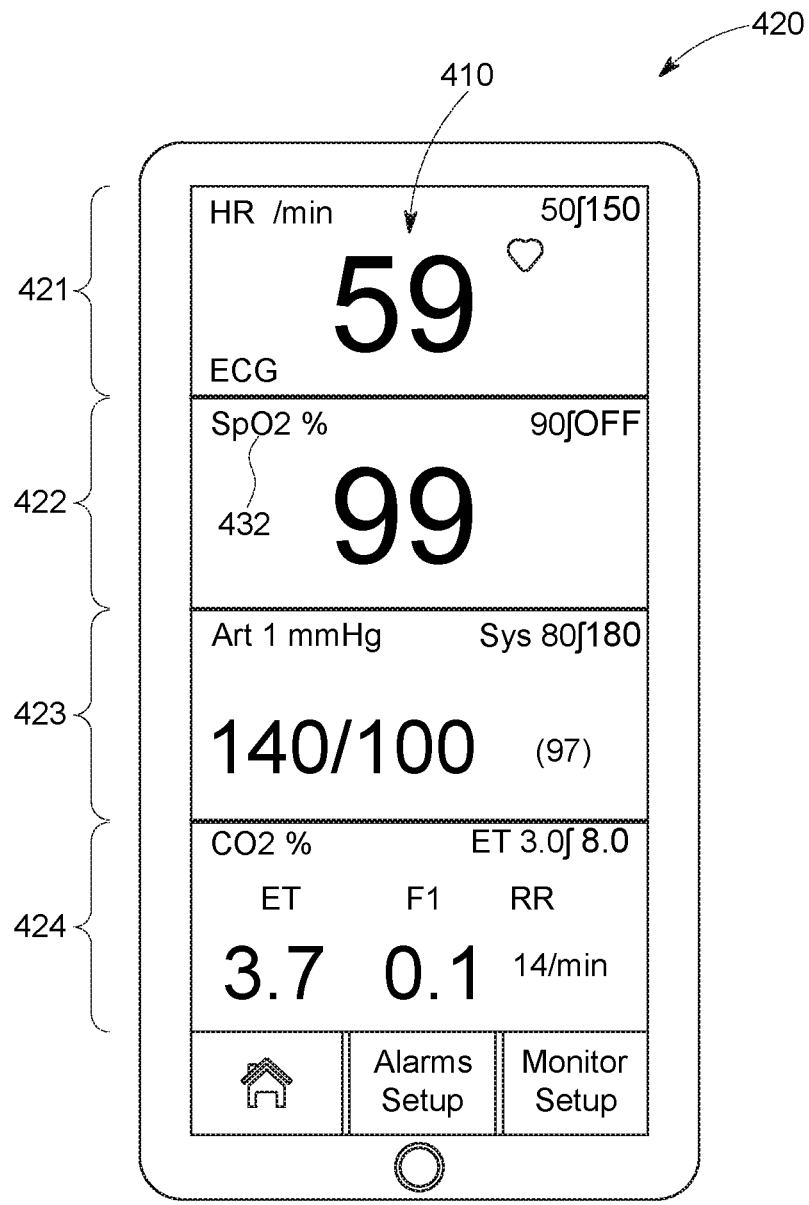
FIG. 12 illustrates a first chart section of a health-monitoring chart that may be presented to a user of a patient-monitoring device in accordance with an embodiment.
Figure 13:
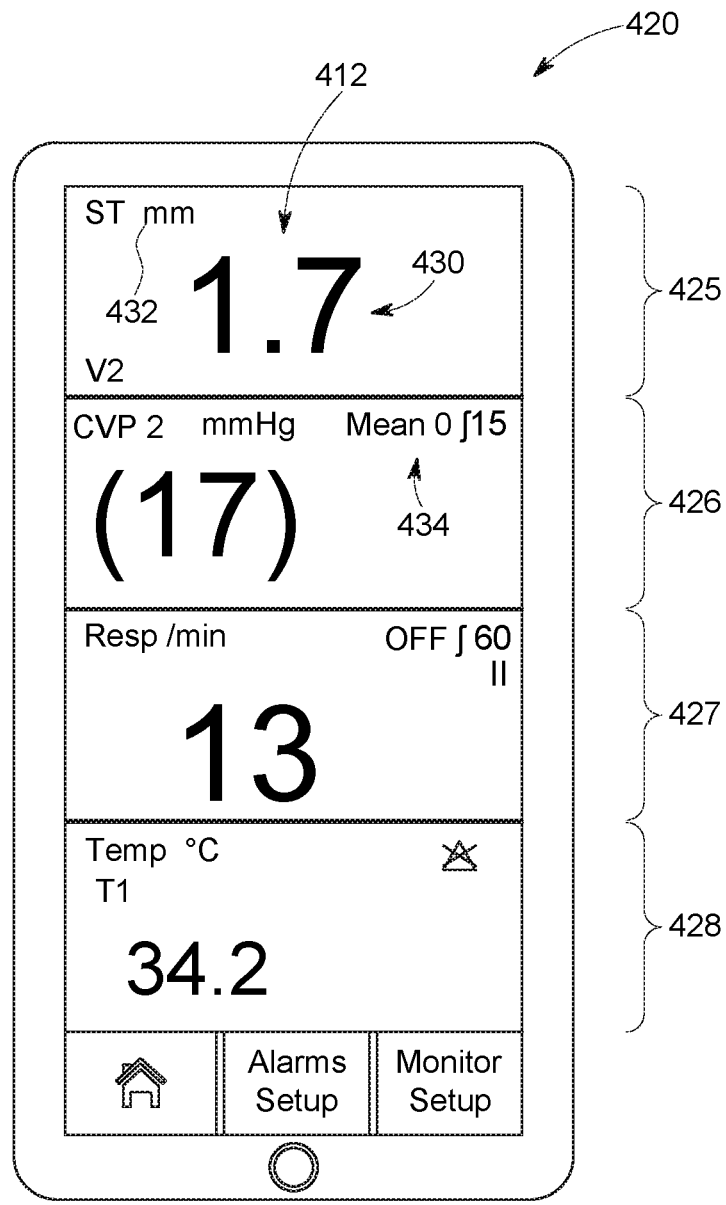
FIG. 13 illustrates a second chart section of a health-monitoring chart that may be presented to a user of a patient-monitoring device in accordance with an embodiment.

FIGS. 12 and 13 show a first chart section 410 and a second chart section 412, respectively, that may be presented to a user of a patient-monitoring device 420, such as a smartphone. As shown, the first chart section 410 does not include parameter signal lines and is arranged upright such that the longest dimension is a vertical dimension. The first chart section 410 includes parameter regions 421-424, and the second chart section 412 includes parameter regions 425-428. Each of the parameter regions 421-428 may include values 430 for the patient parameters, labels 432 identifying the patient parameters, and limits or conditions 434 for the patient parameters. The limits or conditions 434 may be used to determine whether the patient parameter is significant. The parameter regions 421-428 may include additional information, such as a source from which the patient parameter is derived. The first and second chart sections 410, 412 may be transitioned (automatically or manually) in a manner that is similar or identical to the transitions described above.

Figure 14:
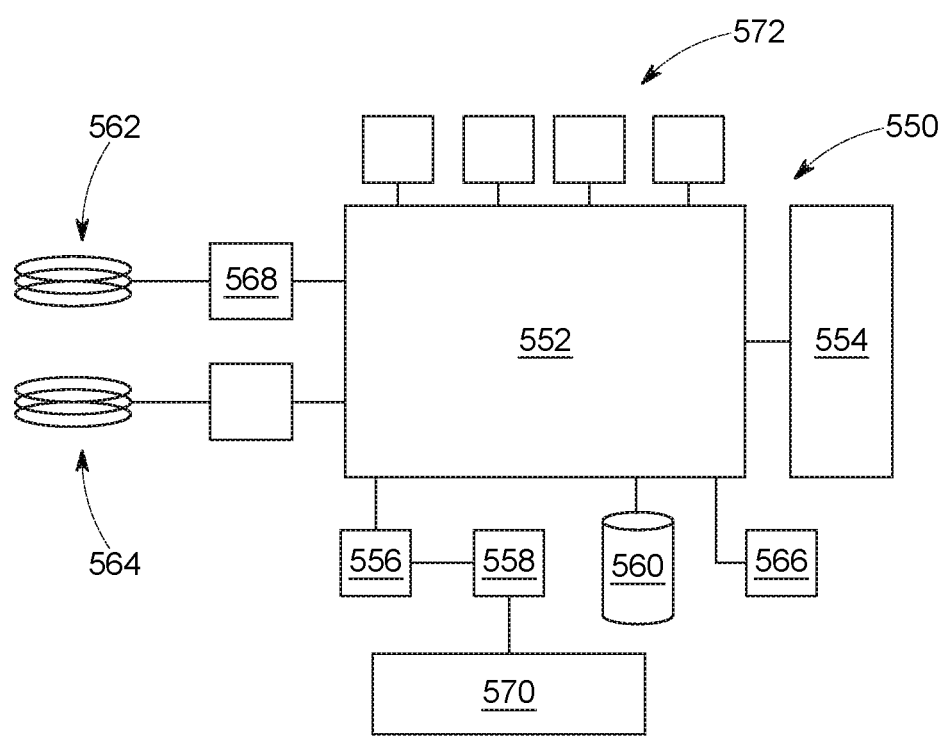
FIG. 14 is a schematic view of a patient-monitoring device in accordance with an embodiment.

FIG. 14 illustrates a block diagram of a patient-monitoring device 550 in accordance with an embodiment. In particular embodiments, the patient-monitoring device 550 is a configured to communicate through a local network of an institution (e.g., healthcare facility, such as a hospital or doctor's office). The local network may include, for example, a wide area network (WAN), a local area network (LAN), campus area network, WIFI, and the like. The patient-monitoring device 550 may be portable and/or hand-held device. In some embodiments, the patient-monitoring device is a proprietary device having custom-designed circuitry, firmware, and/or software that are configured to carry out one or more of the methods set forth herein. In other embodiments, the patient-monitoring device 550 may be an off-the-shelf computing device, such as a tablet computer, that has an application program installed therein to carry out one or more of the methods set forth herein.

The patient-monitoring device 550 may include, among other things, a processor 552, a power management unit (PMU) 554, a gesture recognizer 556, a touchscreen controller 558, memory 560, an antenna 562, one or more other antenna 564 (e.g., cellular, Bluetooth), and one or more secure elements (e.g., embedded, removable) 566. The antenna 562 is communicatively coupled to the processor 552 using a short-range controller 568, which manages emission and reception of signals, among other things. The short-range controller 568 and the antenna 562 may be configured to communicate in accordance with a designated short-range wireless communication technology, such as NFC. The touchscreen controller 558 communicatively couples a touchscreen 570 to the host processor 552. The touchscreen controller 558 is configured to detect touch events and communicate the touch events to the gesture recognizer 556. The gesture recognizer 556 may identify the input gesture based on the touch events and communicate the input gesture to one or more programs implemented by the device.

The memory 560 may store programmed instructions that are accessible to the processor 552 and/or other processors of the device 550. In response to execution of the programmed instructions, the device 500 is configured to perform certain processes, such as the methods set forth herein. Optionally, the patient-monitoring device 550 also includes a plurality of ports 572 (e.g., electrical and/or optical connectors) that are configured to mate with respective plugs or receptacles from other devices, such as the detection devices described herein. The ports 572 are coupled to the processor 552. In some embodiments, the processor 552, another processor, or other circuitry may determine whether the patient parameters are significant using the physiological data provided through the ports 572 and/or through the antenna 562, 564.

Figure 15:
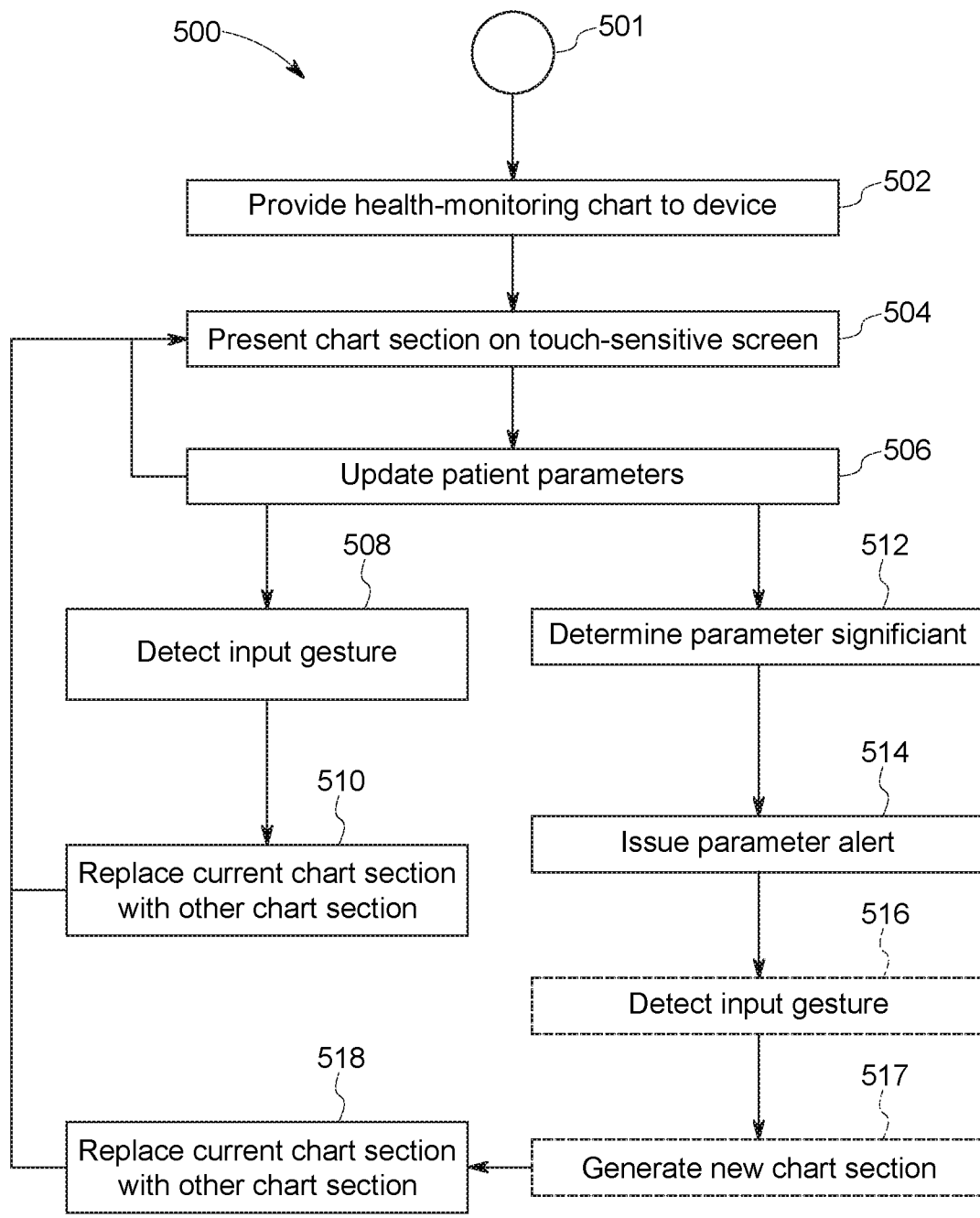
FIG. 15 is a block diagram illustrating a method in accordance with an embodiment.

FIG. 15 illustrates a method 500 in accordance with an embodiment. The method 500 may be performed, at least in part, by embodiments set forth herein. For example, the system 100 may be used to perform the method 500. Although the flow chart in FIG. 15 illustrates individual operations, it should be understood that the operations are not necessarily executed at separate times or in the order shown. An application program on the device may be initiated, at 501, by the user or by a system. The method 500 may include providing (e.g., by the application program) a health-monitoring chart at 502. The health-monitoring chart may be provided to, for example, a patient-monitoring device (e.g., a computing device, such as a portable computer, tablet computer, or smartphone).

The patient-monitoring device has a touchscreen with a display area. For embodiments in which the device is similarly sized to a tablet computer or laptop, the display size (corner-to-corner measurement) may be between 12 centimeters (cm) and 25 cm or larger. For embodiments in which the device is a smart phone, the display area may have a display size that is between 8.5 cm and 15 cm. The aspect ratio for the display area may be between, for example, 5:4 and 4:1. Examples of resolutions for the display include wide video graphics array (WVGA): 800×600; wide super VGA (WSVGA): 1024×600; extended graphics array (XGA): 1024×768; wide XGA (WXGA): 1280×800 or 1366×768; WXGA+: 1440×900; WSXGA+: 1600×900; widescreen ultra XGA (WUXGA): 1920×1080 or 1920×

1200; quad XGA (QXGA): 2048×1536; wide quad high definition (WQHD): 2560×1440 or 2560×1600; and ultra (UHD): 3180×2160.

The health-monitoring chart includes multiple chart sections (or pages). The application program may determine a display area of the device and generate multiple chart sections based on the display area. For example, the application program may determine (e.g., through user inputs or by identifying the detection devices that are coupled to the patient-monitoring device) the number of parameter regions to be shown in the chart sections. Each of the parameter regions may have a predetermined acceptable size for displaying to healthcare providers. For example, a heart rate may have a minimum size for displaying to healthcare providers. Embodiments may determine the size and aspect ratio of the display area and the number and identity of the patient parameters to be displayed and then determine a layout of the patient parameters for each of the chart sections.

In some embodiments, the layouts of the chart sections are based on a priority assigned to the patient parameters. For example, the higher priority parameters may be assigned to the first chart section, and the lower priority parameters may be assigned to subsequent chart sections.

The health-monitoring chart may include a predetermined first chart section and a predetermined second chart section that will be displayed to the user during operation. Alternatively, the health-monitoring chart may include the predetermined first chart section and the second chart section is only generated after determining that a patient parameter has become significant. In other words, the second chart section may be a condition-specific chart section. Depending on the number of patient parameters that are to be shown, the health-monitoring chart may include additional predetermined chart sections (e.g., a third chart section, a fourth chart section, and so forth). During operation, the first and second chart sections may be displayed in accordance with a predetermined routine. For example, the first chart section may be shown for a designated time period (e.g., five seconds) and then the second chart section may replace the first chart section and be shown for a designated time period (e.g., five seconds). Alternatively, a chart section will remain in the display area until changed by the user or a patient parameter of the other chart section is determined to be significant.

The first and second chart sections have parameter regions. The parameter regions may include respective parameter signal lines plotted with respect to horizontal and vertical axes. The horizontal axis represents time and the vertical axis represents a patient parameter of the parameter region that is based on physiological data. The parameter regions of the first and second chart sections may include respective value areas that are aligned with the respective parameter signal lines of the parameter regions. The respective value area indicates a present value of the patient parameter. Alternatively, parameter regions may include only signal lines (or some other non-numerical representation) or only value areas.

The method includes presenting, at 504, a chart section (e.g., the first chart section) on the touchscreen while the other chart section or sections (e.g., the second chart section) is/are not presented on the touchscreen. As the first chart section is presented, the method may operate in real-time such that the device continuously or near continuously receives physiological data from the detection devices and updates, at 506, the patient parameters.

At 508, the touchscreen may detect an input gesture for transitioning to the other chart section. For example, the input gesture may be indicative of a swipe along the touchscreen. The input gesture may extend generally in a swipe direction for at least a predetermined distance along the touchscreen. In other embodiments, a different type of input gesture may be detected. At 510, the health-monitoring chart transitions, in response to detecting the input gesture at 508, the first chart section from the touchscreen and the second chart section into the touchscreen such that the second chart section is presented on the touchscreen and the first chart section is not presented on the touchscreen.

The transition from the first chart section to the second chart section is visually indicated to the user. For example, section identifiers may indicate a total number of chart sections and the current chart section. As shown in FIG. 3, the section identifiers 231, 232 indicate that the chart section is the first chart section of two possible chart sections including patient parameters that are presently being monitored. In some embodiments, the first chart section may appear to move and the second chart section may appear to move during the transition. For example, the transition may include shifting one chart section while causing the other chart section to appear. The transition may also include moving the chart sections (or active fields of the chart sections) as discrete units. The transition may also include audible and/or tactile indications of the transition. Multiple features may be used to indicate the transition. For example, during a single transition, (a) the first chart section may appear to shift out of view and the second chart section may appear to move into view; (b) an audible sound may indicate the transition; and (c) the section identifiers may change, thereby indicating a different chart section is being displayed. The method may return to presenting, at 504, the chart section, but the chart section now presented is the second chart section.

In some embodiments, the health-monitoring chart may automatically transition between the different chart sections in accordance with a predetermined protocol. For example, the health-monitoring chart may present the first chart section for a designated time period and then present the second chart section for a designated time period. As such, at least some embodiments may transition, at 510, without detecting an input gesture.

The method may also include determining, at 512, that a patient parameter is significant. For example, it may be determined that the heart rate is too high or too low. The patient parameter may be displayed in the current chart section or may be a part of the hidden chart section. In response to determining that a patient parameter is significant, the method 500 includes issuing, at 514, a parameter alert. The parameter alert may be displayed on the chart section and be visually distinguishable from a surrounding area. The parameter alert does not appear when the patient parameter is not significant.

At 516, an input gesture may be detected. The input gesture may instruct the device to present the hidden chart section (or condition-specific chart section as described below). For example, if the heart rate is excessive, the user may double tap the parameter region that includes the heart rate or may double tap the parameter alert.

Optionally, at 517, a condition-specific chart section may be generated. The condition-specific chart section has a different arrangement of parameter regions than the predetermined chart section or chart sections. The new arrangement of parameter regions may be based on a suspected condition. More specifically, the significant patient parameter may indicate that the patient has a condition (suspected condition). The condition-specific chart section may provide more information and/or present the information in a more readily readable manner for determining whether the patient has the suspected condition. In some cases, a different group of parameter regions may be displayed. The condition-specific chart section may include the patient parameter that was determined to be significant and other patient parameters that may be used for assessing the suspected condition.

At 518, the health-monitoring chart may transition from the current or displayed chart section to another chart section. If a condition-specific chart section was generated, the health-monitoring chart transitions from the displayed chart section to the condition-specific chart section. Otherwise, the health-monitoring chart may transition to the chart section having the patient parameter that is significant. The method 500 may then present the chart section at 504 and update the patient parameters in the chart section at 506.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A handheld patient-monitoring device comprising:
    a touchscreen having a display area and configured to present a health-monitoring chart to a user, the health-monitoring chart being based on physiological data detected from a patient;
    one or more processors configured to execute programmed instructions stored in memory, the one or more processors, when executing the programmed instructions, configured to:
        present a first chart section of the health-monitoring chart in the display area of the touchscreen, the first chart section having parameter regions that include information relating to respective patient parameters of the patient;
        determine that one of the patient parameters has become significant;
        in response to determining that one of the patient parameters has become significant, generate a second chart section of the health-monitoring chart based on the patient parameter that has become significant, the second chart section including the patient parameter that has become significant and one or more additional patient parameters that are not presented in the first chart section and are associated with a predetermined condition, wherein the second chart section includes a parameter signal line plotted with respect to horizontal and vertical axes, the horizontal axis representing time and the vertical axis representing values of the patient parameter that has become significant;
        detect an input gesture on the touchscreen that is indicative of a swipe along the touchscreen, the input gesture extending in a swipe direction for at least a predetermined distance along the touchscreen; and
        in response to detecting the input gesture, replace the first chart section with the second chart section such that the second chart section is presented in the display area and the first chart section is not presented in the display area, wherein replacement of the first chart section with the second chart section is visually indicated to the user.

2. The patient-monitoring device of claim 1, wherein the one or more processors are further configured to display a parameter alert on the first chart section, the parameter alert identifying the patient parameter that has become significant.

3. The patient-monitoring device of claim 1, wherein the one or more processors are configured to select the additional patient parameters included in the second chart section for assessing whether the patient has the predetermined condition.

4. The patient-monitoring device of claim 1, wherein the patient parameter that has become significant is highlighted to the user in the second chart section.

5. The patient-monitoring device of claim 1, wherein the one or more processors are further configured to indicate that the first chart section is shifting in the swipe direction when replacing the first chart section with the second chart section.

6. The patient-monitoring device of claim 1, wherein the first chart section and the second chart section appear as separate and discrete sections.

7. A method for monitoring a condition of a patient, the method comprising:
    providing a health-monitoring chart to a patient-monitoring device for presenting in a display area of a touchscreen of the patient-monitoring device, the health-monitoring chart including a first chart section and a second chart section;
    presenting the first chart section in the display area of the touchscreen, the first chart section having parameter regions that include information relating to respective patient parameters of the patient;

determining that one of the patient parameters has become significant;

in response to determining that one of the patient parameters has become significant, generating the second chart section based on the patient parameter that has become significant, the second chart section including the patient parameter that has become significant and one or more additional patient parameters that are not presented in the first chart section and are associated with a predetermined condition, wherein the second chart section includes a parameter signal line plotted with respect to horizontal and vertical axes, the horizontal axis representing time and the vertical axis representing values of the patient parameter that has become significant;

detecting an input gesture on the touchscreen that is indicative of a swipe along the touchscreen, the input gesture extending in a swipe direction for at least a predetermined distance along the touchscreen; and in response to detecting the input gesture, replacing the first chart section with the second chart section such that the second chart section is presented in the display area and the first chart section is not presented in the display area, wherein replacement of the first chart section with the second chart section is visually indicated to the user.

8. The method of claim 7, further comprising displaying a parameter alert on the first chart section, the parameter alert identifying the patient parameter that has become significant.

9. The method of claim 7, further comprising selecting the additional patient parameters included in the second chart section for assessing whether the patient has the predetermined condition.

10. The method of claim 7, wherein the patient parameter that has become significant is highlighted to the user in the second chart section.

11. The method of claim 7, wherein the first chart section and the second chart section appear as separate and discrete sections.

12. A non-transitory computer-readable storage medium having computer executable code to:

present a first chart section of a health-monitoring chart of a patient in a display area of a touchscreen, the first chart section having parameter regions that include information relating to respective patient parameters of the patient;

determine that one of the patient parameters has become significant;

in response to determining that one of the patient parameters has become significant, generate a condition-specific chart section of the health-monitoring chart based on the patient parameter that has become significant, the condition-specific chart section including the patient parameter that has become significant and one or more additional patient parameters that are not presented in the first chart section and are associated with a predetermined condition, wherein the condition-specific chart section includes a parameter signal line plotted with respect to horizontal and vertical axes, the horizontal axis representing time and the vertical axis representing values of the patient parameter that has become significant;

receive an input gesture from a gesture recognizer that is indicative of a swipe along the touchscreen;

in response to receiving the input gesture, replace the first chart section with the condition-specific chart section such that the condition-specific chart section is presented in the display area and the first chart section is not presented in the display area; and indicate, in the display area, that the condition-specific chart section has replaced or is replacing the first chart section.

13. The computer-readable storage medium of claim 12, wherein the computer executable code is also configured to display a parameter alert on the touchscreen with the first chart section responsive to determining that one of the patient parameters of the first chart section has become significant, the parameter alert identifying the patient parameter that has become significant.

14. The computer-readable storage medium of claim 12, wherein the first chart section and the condition-specific chart section appear as separate and discrete sections.

15. The computer-readable storage medium of claim 12, wherein the determination that the patient parameter has become significant is based on one or more of: (i) the patient parameter being above a designated upper limit; (ii) the patient parameter being below a designated lower limit; or (iii) the patient parameter being outside of a designated operating range.

16. The handheld patient-monitoring device of claim 1, wherein the second chart section is associated with the predetermined condition and the additional patient parameters included in the second chart section are selected for assessing whether the patient has the predetermined condition.

17. The handheld patient-monitoring device of claim 1, wherein the patient parameter that has become significant is a heart rate of the patient, and the predetermined condition is a cardiac condition.

* * * * *